(12) United States Patent
Gao et al.

(10) Patent No.: US 11,643,436 B2
(45) Date of Patent: May 9, 2023

(54) POLYPEPTIDE COMPOUND, PHARMACEUTICAL COMPOSITION, PREPARATION METHOD AND APPLICATION THEREOF

(71) Applicant: CHENGDU SINTANOVO BIOTECHNOLOGY CO., LTD., Sichuan (CN)

(72) Inventors: Jian Gao, Sichuan (CN); Xiaoping Fu, Sichuan (CN); Guoqing Zhong, Sichuan (CN); Haibo Zhou, Sichuan (CN); Hai Hu, Sichuan (CN); Xi Hu, Sichuan (CN); Yu Yuan, Sichuan (CN); Yuanbo Li, Sichuan (CN); Sijun Li, Sichuan (CN)

(73) Assignee: CHENGDU SINTANOVO BIOTECHNOLOGY CO., LTD., Sichuan (CN)

( * ) Notice: Subject to any disclaimer, the term of this patent is extended or adjusted under 35 U.S.C. 154(b) by 0 days.

(21) Appl. No.: 17/093,607

(22) Filed: Nov. 9, 2020

(65) Prior Publication Data

US 2021/0139537 A1    May 13, 2021

(30) Foreign Application Priority Data

Nov. 12, 2019 (CN) .......................... 201911100565.6
Mar. 11, 2020 (CN) .......................... 202010165892.6

(51) Int. Cl.
*C07K 5/107*     (2006.01)
*C07K 5/02*      (2006.01)

(52) U.S. Cl.
CPC .......... *C07K 5/1016* (2013.01); *C07K 5/0202* (2013.01)

(58) Field of Classification Search
None
See application file for complete search history.

(56) References Cited

U.S. PATENT DOCUMENTS

| | | | |
|---|---|---|---|
| 7,056,942 B2 * | 6/2006 | Hildesheim | ............. A61P 43/00 514/411 |
| 2006/0089312 A1 | 4/2006 | Bachovchin | |
| 2006/0276435 A1 | 12/2006 | Cohen et al. | |
| 2007/0099917 A1 * | 5/2007 | Nice | ........................ A61P 35/00 514/234.2 |
| 2009/0264373 A1 | 10/2009 | Schteingart et al. | |
| 2016/0194358 A1 | 7/2016 | Smith | |
| 2018/0282369 A1 | 10/2018 | Desai et al. | |
| 2019/0144498 A1 | 5/2019 | Urban et al. | |
| 2019/0144499 A1 | 5/2019 | Li | |
| 2020/0109166 A1 | 4/2020 | Cai et al. | |

FOREIGN PATENT DOCUMENTS

| | | | |
|---|---|---|---|
| CN | 101535336 A | | 9/2009 |
| CN | 105636978 A | | 6/2016 |
| CN | 107098871 A | | 8/2017 |
| CN | 107098876 A | | 8/2017 |
| CN | 109879934 A | | 6/2019 |
| CN | 110790817 | * | 2/2020 |
| CN | 110790817 A | | 2/2020 |
| CN | 111233974 A | | 6/2020 |
| EP | 2204181 A2 | | 7/2010 |
| EP | 3521301 A1 | | 8/2019 |
| WO | 2006125227 A2 | | 11/2006 |
| WO | 2013184794 A2 | | 12/2013 |
| WO | 2016181408 A2 | | 11/2016 |
| WO | 2017211272 A1 | | 12/2017 |
| WO | 2017214076 A1 | | 12/2017 |
| WO | 2018059331 A1 | | 4/2018 |

OTHER PUBLICATIONS

Vippagunta et al. ('Crystalline solids' Advanced drug delivery reviews v48 2001 pp. 3-26) (Year: 2001).*
Translation of CN110790817 Feb. 2020; retrieved from https://worldwide.espacenet.com/patent/search/family/069444342/publication/CN110790817A?q=cn110790817 on Oct. 20, 2021; 12 total pages (Year: 2021).*
The 1st Office Action dated Sep. 8, 2020 for the Chinese Patent Application No. CN202010165892.6.
The 2nd Office Action dated Oct. 20, 2020 for the Chinese Patent Application No. CN202010165892.6.
The International Search Report and Written Opinion of the International Searching Authority dated Feb. 7, 2021 for PCT/CN2020/127402.
Smoum et al: "Boron containing compounds as protease inhibitors", Chemical Reviews, vol. 112, Apr. 20, 2012, pp. 4156-4220.
The European Search Report dated Apr. 23, 2021 for EP20206521.5.

* cited by examiner

*Primary Examiner* — Ronald T Niebauer
(74) *Attorney, Agent, or Firm* — Yue (Robert) Xu; Apex Attorneys at Law, LLP

(57) ABSTRACT

The present invention discloses a polypeptide compound, a pharmaceutical composition, and a preparation method and use thereof. The structural formula of the polypeptide compound is shown in general formula (I):

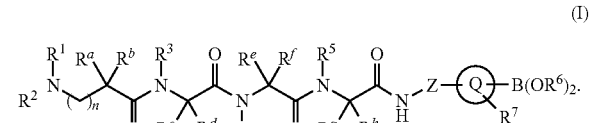

Such polypeptide compounds as κ-opioid receptor agonists have the advantages of better activity and the potential to become clinical candidate compounds.

2 Claims, No Drawings

POLYPEPTIDE COMPOUND, PHARMACEUTICAL COMPOSITION, PREPARATION METHOD AND APPLICATION THEREOF

CROSS REFERENCE TO RELATED APPLICATIONS

This application claims the priority of Chinese Patent Application No. CN201911100565.6, filed on Nov. 12, 2019 and titled with "POLYPEPTIDE COMPOUND, PREPARATION, PHARMACEUTICAL COMPOSITION, PREPARATION METHOD AND APPLICATION", and Chinese Patent Application No. CN202010165892.6, filed on Mar. 11, 2020 and titled with "POLYPEPTIDE COMPOUND, PHARMACEUTICAL COMPOSITION, PREPARATION METHOD AND APPLICATION", and the disclosures of which are hereby incorporated by reference.

FIELD

The present invention relates to the field of medicine, in particular to a polypeptide compound, a pharmaceutical composition, and a preparation method and application thereof.

BACKGROUND

Analgesics are drugs that mainly act on the central or peripheral nervous system, selectively inhibit and relieve various pains, and relieve fear, tension, and anxiety caused by pain. At present, the global analgesic market is dominated by opioids and non-steroidal anti-inflammatory drugs, which together accounted for more than 52% of the total market revenue in 2015. According to a report based on US Transparency Market Research, the global analgesic market will reach 88.2 billion US dollars by the end of 2025.

Opioid receptors are a major type of G protein-coupled receptors, which are the binding targets of endogenous opioid peptides and opioids. The activation of opioid receptors has a regulatory effect on the immunity of the nervous system and the endocrine system. It is currently the strongest and commonly used central analgesic. Endogenous opioid peptides are opioid active substances naturally produced in mammals. The currently known endogenous opioid peptides can be roughly divided into enkephalins, endorphins, dynorphins and neorphins. There are corresponding opioid receptors in the central nervous system, namely μ, δ and κ receptors. The μ receptor has the strongest analgesic activity and the strongest addiction, which is the main cause of side effects. The δ receptor is less addictive, and its analgesic effect is not obvious. The analgesic activity of κ receptor (KOR) lies between the former two. KOR provides a natural addiction control mechanism, therefore, drugs as KOR receptor agonists have the potential to treat drug addiction.

Traditional μ opioid receptor agonists (such as morphine and its derivatives) are the main drugs for clinical relief of severe pain, and are the most used powerful analgesic in the world. They are the most effective drugs for treating chronic arthritis, inflammatory neuralgia, postoperative pain, and moderate to severe pain caused by various cancers. However, systemic administration of traditional μ opioid analgesics can cause side effects, such as respiratory depression, drug addiction, constipation, nausea, confusion, and tolerance. Piperidines (pethidine, fentanyl, etc.) are also μ opioid receptor agonists, which have the same pharmacological effects as morphine and the same clinical application as morphine. However, pethidine has less sedative and anesthetic effects, and has weaker respiratory depression than morphine, and has less adverse reactions than morphine. Other common μ opioid receptor agonists include aminoketones (methadone, dextropropoxyphene), cyclohexane derivatives (tramadol), and aminotetralins (dazocine). There are still many μ opioid receptor agonists in preclinical and clinical stages.

The κ-opioid receptor (KOR) consists of 380 amino acids, and dynorphin is its endogenous ligand. It is expressed in sensory neurons, dorsal root ganglion cells and the terminals of primary afferent neurons, and is related to major physiological activities such as pain, neuroendocrine, emotional behavior and cognition. κ-opioid receptor agonists are different from opioid receptor agonists in that they do not cause respiratory depression and constipation, and studies have shown that they are less addictive. Peripheral administration of opioid receptor agonists does not have any analgesic effect under normal conditions of the body. When there is inflammation or tissue damage, the function of peripheral opioid receptors is enhanced, and it exerts an analgesic effect after the administration of an opioid receptor agonist. In addition, the body is not easily tolerated by κ-opioid receptor agonists.

The blood-brain barrier consists of several parts, mainly including endothelial cells (including a special basement membrane) arranged along the walls of brain capillaries, continuous tight junctions and no-paracellular-transport, as well as adjacent cells and active transport molecules. Due to the nature of this barrier, small lipophilic molecules are more likely to enter the central nervous system, while large lipophilic compounds are less likely to enter the brain. Therefore, the aim of achieving analgesia while avoiding central nervous system penetration is focused on finding large/hydrophilic pharmacophores.

Patent CN101535336A discloses a synthetic peptide amide ligand for κ-opioid receptor. The synthetic peptide amide has high selectivity to the κ-opioid receptor. The pharmaceutical composition containing the compound can be used to prevent and treat pain and inflammation related to various diseases, and has a certain potential for preparing medicine.

Patent WO2013184794 discloses a novel polypeptide κ-opioid receptor agonist. A tetrapeptide with D configuration amino acids is contained in the molecular structure, and has shown strong analgesic activity in clinical trials. The clinical indications that have been initiated include: acute pain, uremia, itching, pain after abdominal surgery, osteoarthritis, sciatic and musculoskeletal diseases, rheumatic diseases, postoperative pain, pruritus, chronic kidney disease and the like. Such peptide drugs have a brand-new mechanism of action, providing an improved treatment method for moderate to severe pain. However, clinical Phase III trials have shown that it can cause some side effects such as hypernatremia.

SUMMARY

The purpose of the present invention is to provide a polypeptide compound, which, as a κ-opioid receptor agonist, has the advantages of better activity and potential to become a clinical candidate compound.

In addition, the present invention also provides compounds prepared from the above-mentioned polypeptide compounds, pharmaceutical compositions, and preparation methods and applications of the polypeptide compounds.

The present invention is carried out through the following technical solutions:

A polypeptide compound is provided, the polypeptide compound has a structural formula as shown in general formula (I):

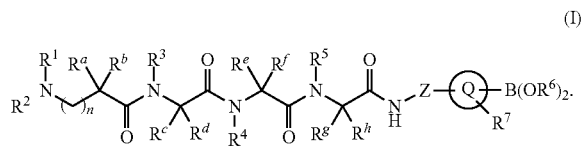

(I)

wherein n is any integer from 0 to 3;

wherein $R^1$ and $R^2$ are selected from hydrogen, alkyl, alkoxy, haloalkyl, cycloalkyl, cycloalkylalkyl, heterocycloalkyl, aryl, arylalkyl, heteroaryl, phthaloyl, p-toluenesulfonyl, o-nitrobenzenesulfonyl, p-nitrobenzenesulfonyl, tert-butoxycarbonyl, benzyloxycarbonyl, 9-fluorenylmethyloxycarbonyl, allyloxycarbonyl, trimethylsilylethyloxycarbonyl, C1-C8 alkoxycarbonyl, C1-C8 acyl, trifluoroacetyl, arylformyl, trityl, benzyl, 2,4-dimethoxybenzyl and p-methoxybenzyl, wherein the heterocycloalkyl and heteroaryl contain 1 to 4 heteroatoms selected from N, O, and S;

wherein the alkyl, alkoxy, haloalkyl, cycloalkyl, cycloalkylalkyl, heterocycloalkyl, heterocycloalkylalkyl, aryl, arylalkyl, heteroaryl, and heteroarylalkyl can be substituted by one or more substituents selected from alkyl, alkoxy, haloalkyl, cycloalkyl, cycloalkylalkyl, heterocycloalkyl, heterocycloalkylalkyl, aryl, arylalkyl, heteroaryl, heteroarylalkyl, alkenyl, alkynyl, hydroxyl, amino, nitro, cyano, carboxyl, ester group, acylamino, mercapto, amidino, and ureido;

wherein $R^3$, $R^4$, $R^5$, $R^a$, $R^c$, $R^e$ and $R^g$ are selected from hydrogen and C1-C10 alkyl.

wherein $R^b$, $R^d$, $R^f$ and $R^h$ are selected from hydrogen, alkyl, alkoxy, haloalkyl, cycloalkyl, cycloalkylalkyl, heterocycloalkyl, aryl, arylalkyl, heteroaryl, alkenyl, alkynyl, hydroxyl, amino, nitro, cyano, carboxy, ester group, acylamino, mercapto, amidino and ureido, wherein the heterocycloalkyl and heteroaryl contain 1 to 4 heteroatoms selected from N, O, and S;

wherein the alkyl, alkoxy, haloalkyl, cycloalkyl, cycloalkylalkyl, heterocycloalkyl, heterocycloalkylalkyl, aryl, arylalkyl, heteroaryl, heteroarylalkyl, alkenyl, and alkynyl can be substituted by one or more substituents selected from alkyl, alkoxy, haloalkyl, cycloalkyl, cycloalkylalkyl, heterocycloalkyl, heterocycloalkylalkyl, aryl, arylalkyl, heteroaryl, heteroarylalkyl, alkenyl, alkynyl, hydroxyl, amino, nitro, cyano, carboxyl, ester group, sulfonyl, sulfinyl, phosphoryl, phosphinyl, phosphate (phosphite), acylamino, mercapto, amidino and ureido;

wherein Z is a bond, optionally substituted C1-C12 alkyl, C1-C8 cycloalkyl, aryl, saturated or unsaturated heterocyclic ring;

wherein $R^7$ is H, hydroxyl, amino, halogen, alkenyl, alkynyl, ester group, acylamino, nitro, cyano, mercapto, optionally substituted C1-C12 alkyl, C1-C8 cycloalkyl, aryl, saturated or unsaturated heterocyclic ring;

wherein $B(OR^6)_2$ is any one of the following substituents, and a part of atoms in two $R^6$ groups can be connected to form a cyclic substituent:

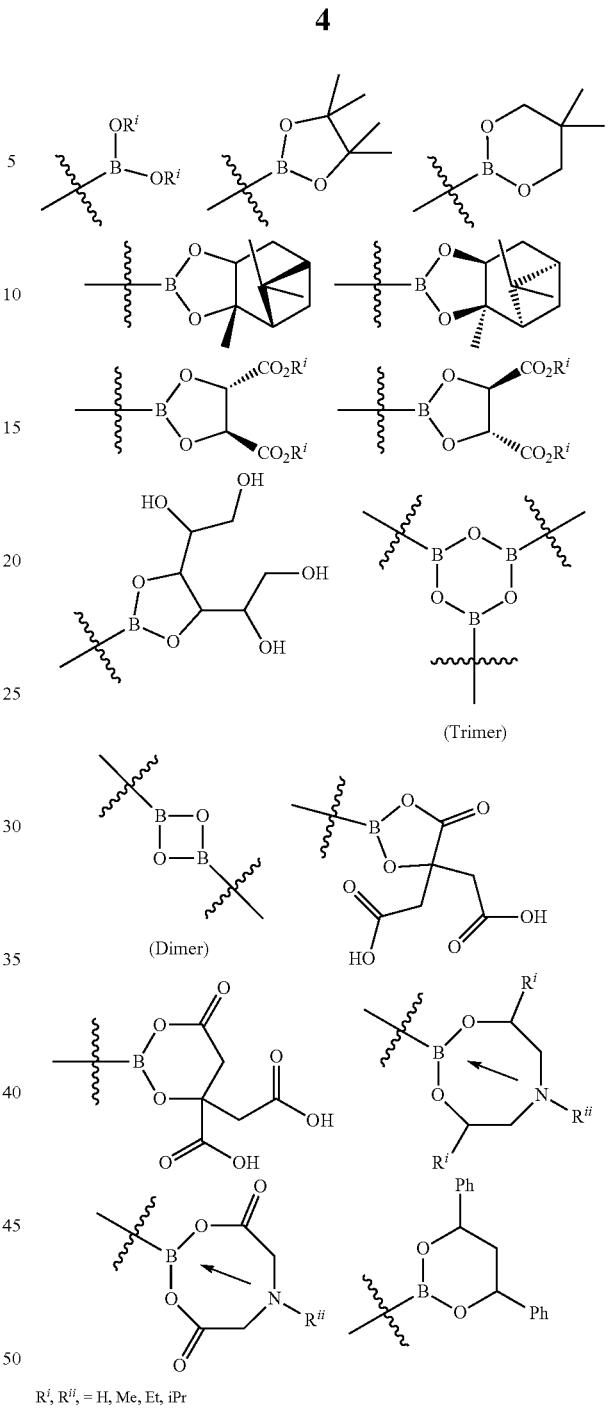

wherein (Q)

is selected from optionally substituted 3- to 8-membered saturated or unsaturated carbocyclic ring, heterocyclic ring, or bridged-ring, spiro-ring, and fused-ring comprising the carbocyclic ring and heterocyclic ring, wherein the heterocyclic ring contains 1 to 3 heteroatoms selected from N, O and S, wherein

is optionally substituted by a group selected from C1-C12 alkyl, cycloalkyl, cycloalkylalkyl, heterocycloalkyl, heterocycloalkylalkyl, aryl, arylalkyl, heteroaryl, heteroarylalkyl, alkenylalkyl, alkynylalkyl, ester group, acylamino, halogen, nitro, cyano, mercapto, hydroxyl, alkoxy, amino, alkenyl and alkynyl; or

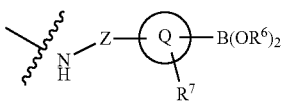

includes but is not limited to the following structures:

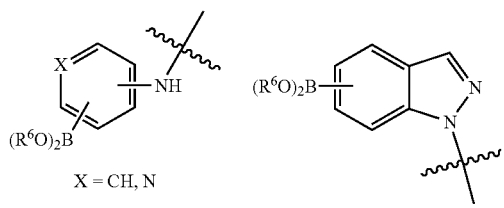

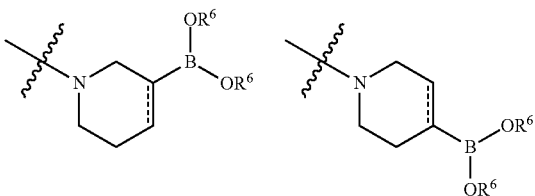

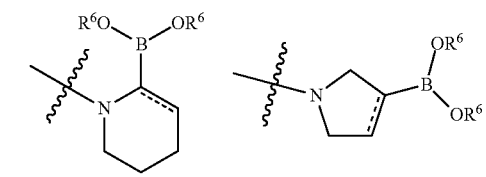

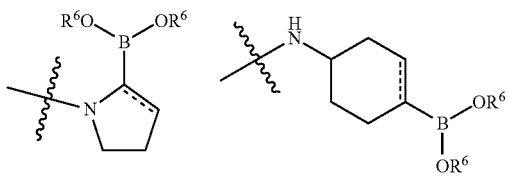

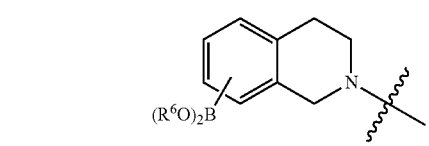

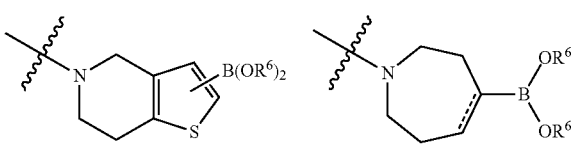

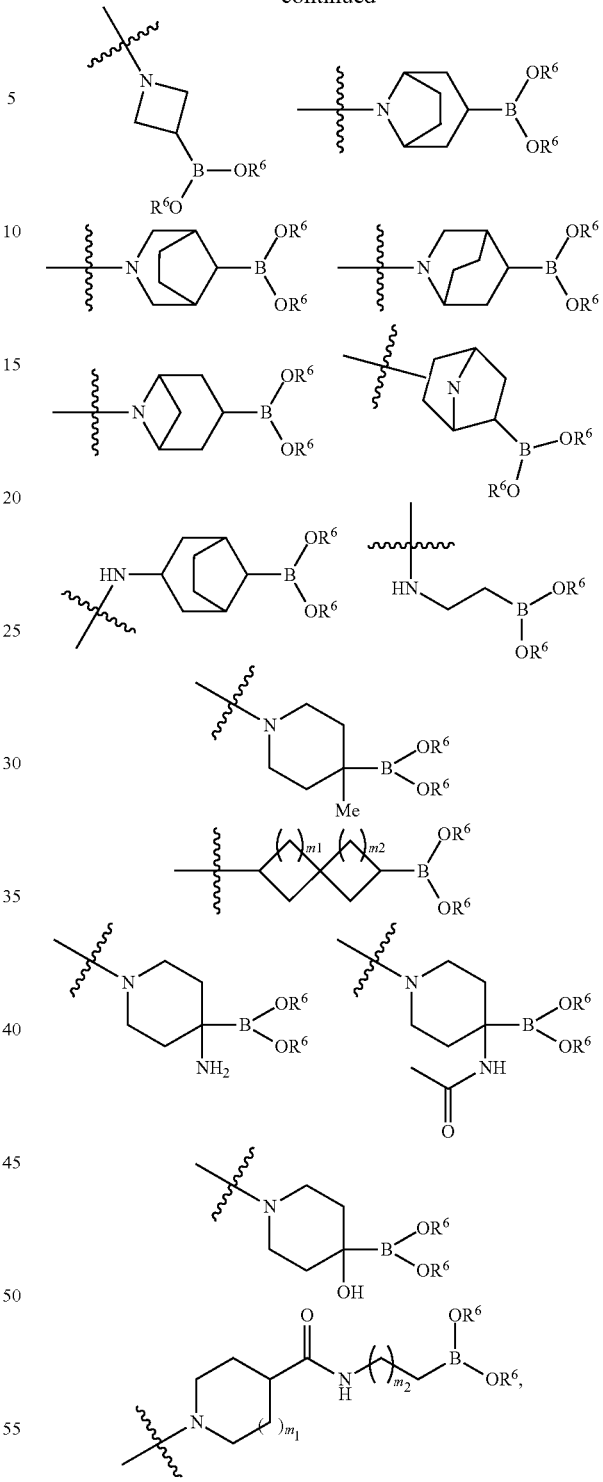

wherein $m_1$ and $m_2$ are any integers from 0 to 6.

The polypeptide compounds of the present invention are novel polypeptide derivatives containing boric acid structural fragments, wherein boron-containing compounds have delicate characteristics, which can reversibly interact with protein targets. Using polypeptide derivatives obtained by combining boric acid groups with polypeptides as a κ-opioid receptor agonist drug has better analgesic activity.

Preferably, in the general formula (I), R1 together with one or more atoms in $R^2$, $R^a$ and $R^b$ forms a ring, including but not limited to the following groups:

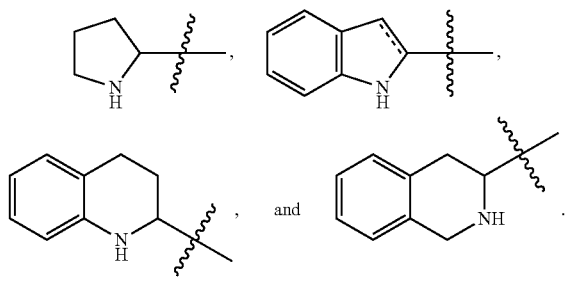

Preferably, in the general formula (I), $R^h$ is selected from any one of the following substituents:

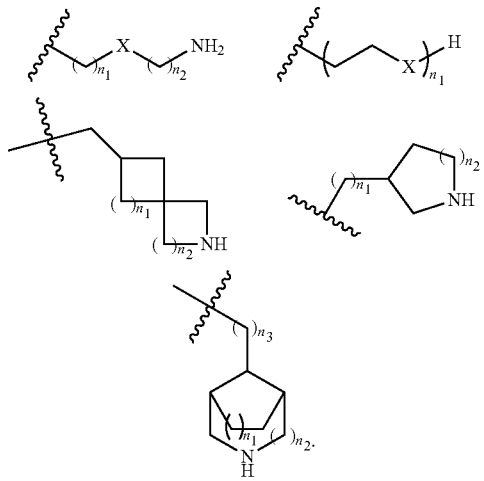

wherein the substituents in the above structural formula are substituted by one or more groups selected from H, halogen, C1-C10 alkyl, C1-C10 alkoxy, C1-C10 haloalkyl, amino, hydroxyl, cyano, nitro, acylamino, ester group, sulfonyl, sulfinyl, phosphoryl, phosphinyl, phosphate group, phosphite group, 3-10 membered heterocyclic group, C1-C10 cycloalkyl, C6-C14 aryl and C5-C15 heteroaryl, wherein X is $CH_2$, NH, O or S; $n_1$, $n_2$ and $n_3$ are any integers from 0 to 3.

Preferably, in the general formula (I), $R^1$, $R^2$, $R^b$, $R^d$, $R^f$, and $R^h$ are further substituted with one or more W groups, wherein W is selected from C1-C10 alkyl substituted by one to ten hydroxy, amino or sulfhydryl; monosaccharides; polysaccharides composed of 2-20 different or same monosaccharides; and optionally substituted oligoethylene glycol.

Preferably, the polypeptide compound has a structural formula as shown in general formula (II):

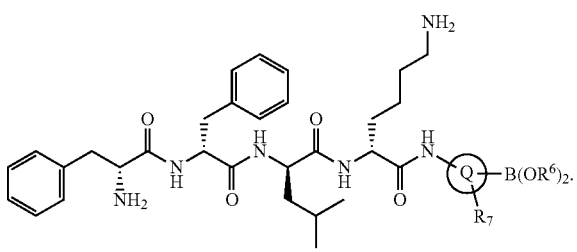

The general formula (II) includes but is not limited to:

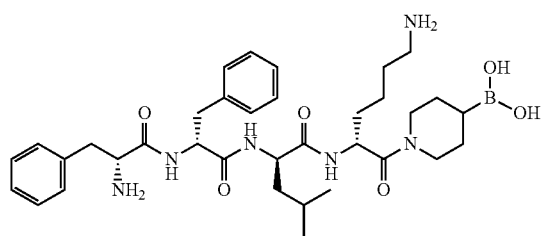

TM-1

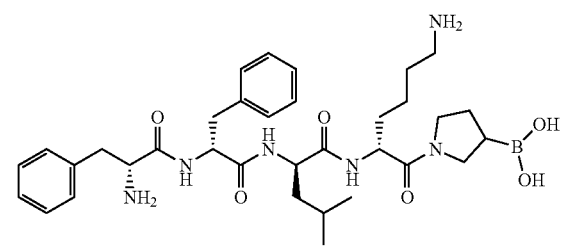

TM-2

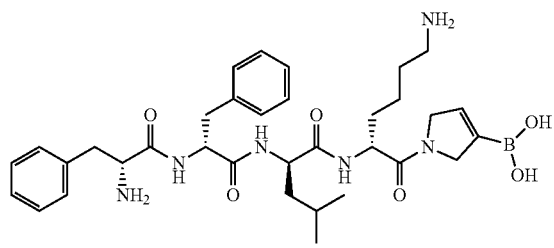

TM-3

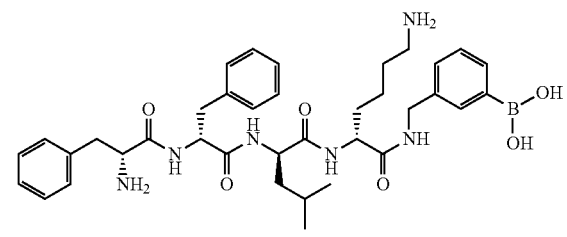

TM-4

-continued
TM-5
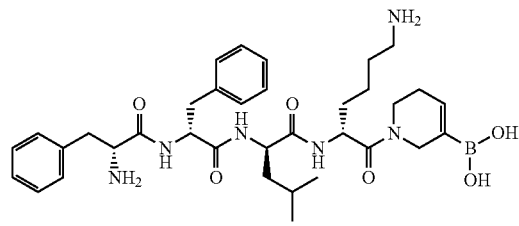
TM-6
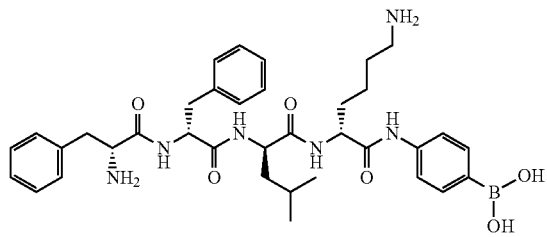
TM-7
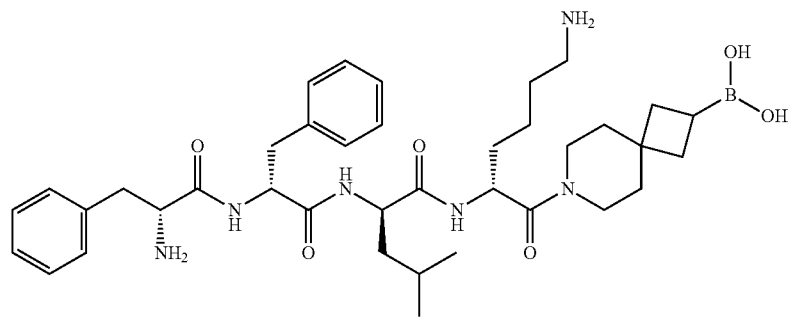
TM-8
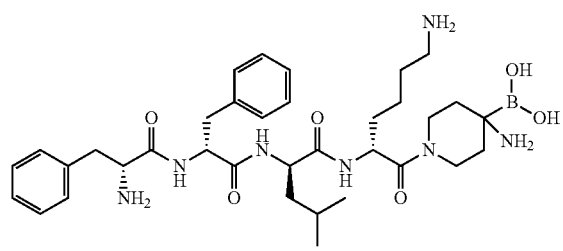
TM-9
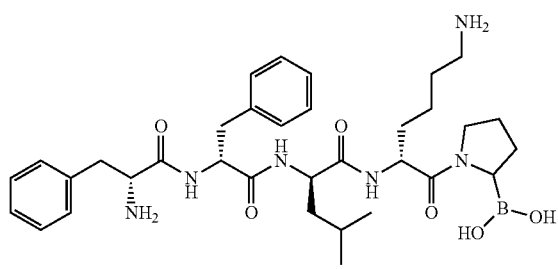
TM-10
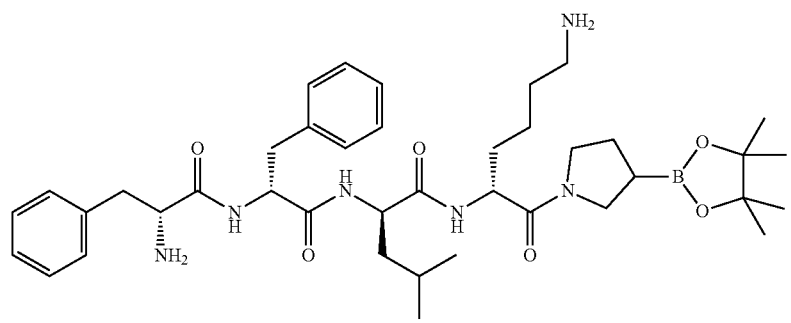
TM-11
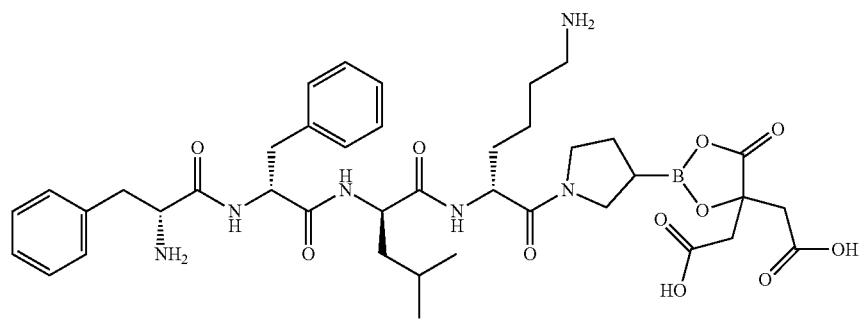

-continued
TM-12
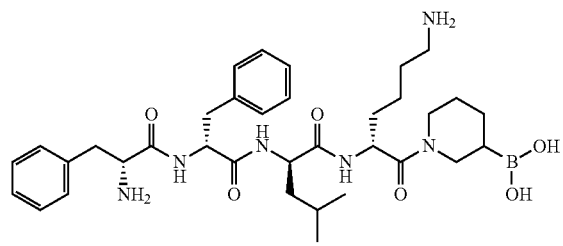
TM-13
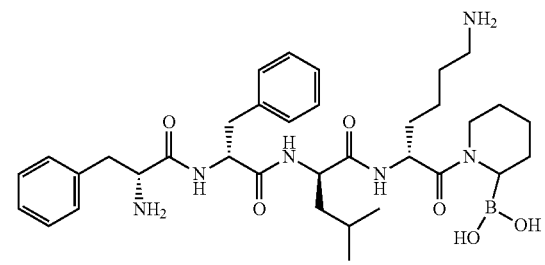
TM-14
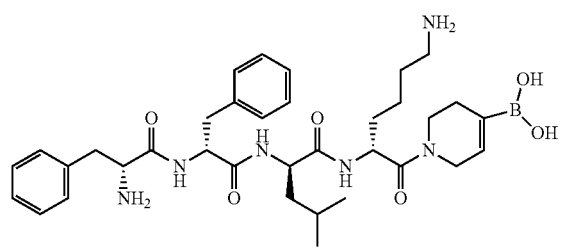
TM-15
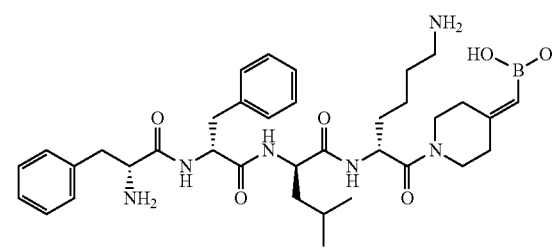
TM-16
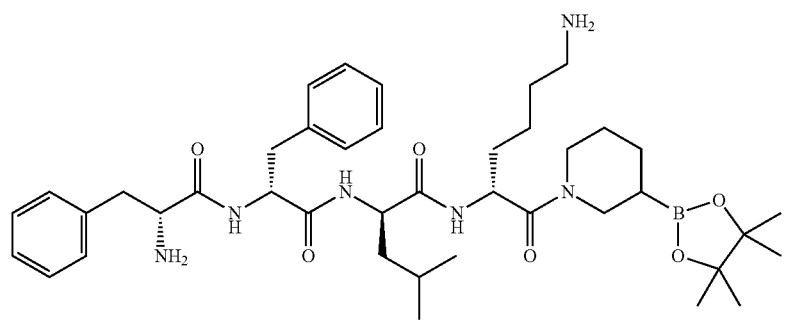
TM-17
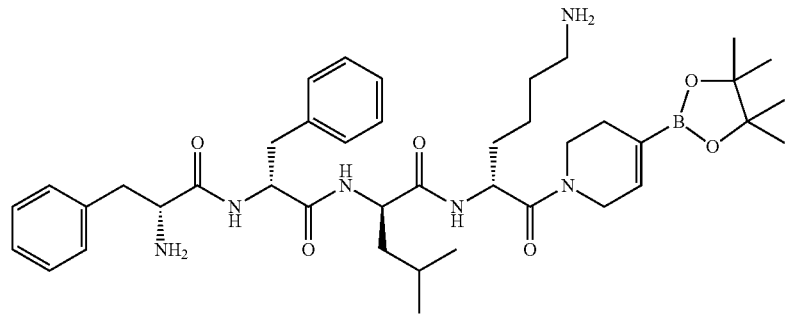
TM-18
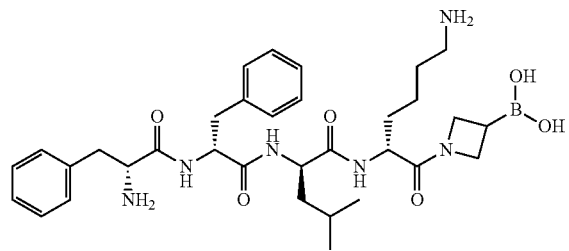
TM-19
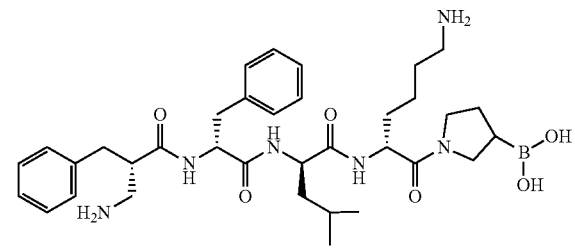

-continued
TM-20
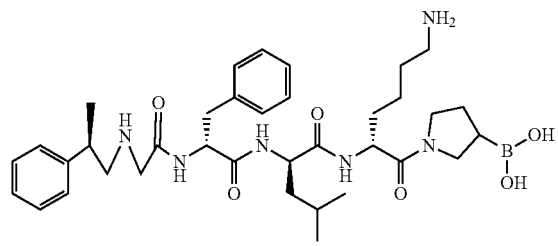
TM-21
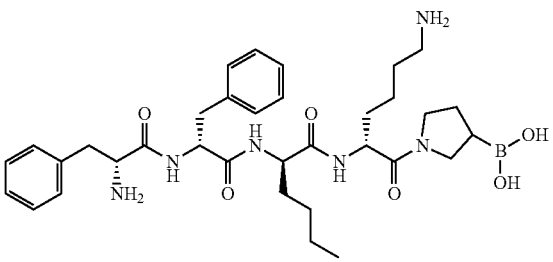
TM-22
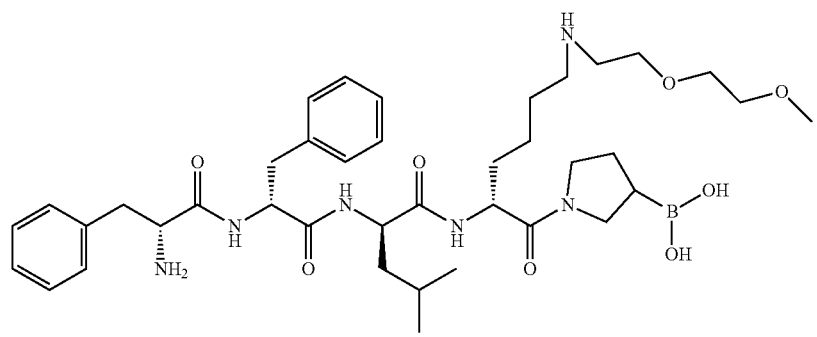
TM-23
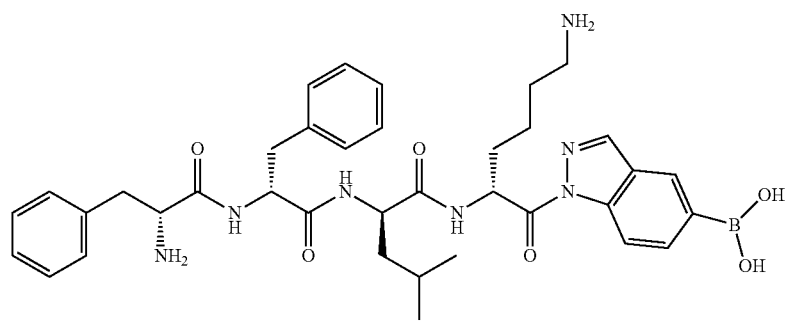
TM-24
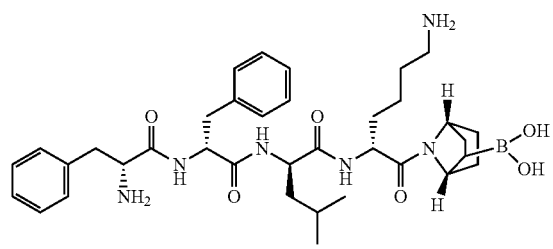
TM-25
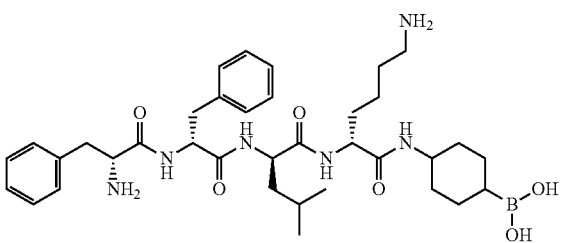
TM-26
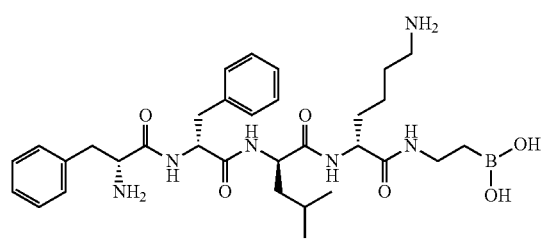
TM-27
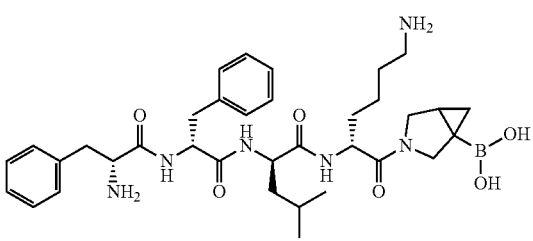

TM-28
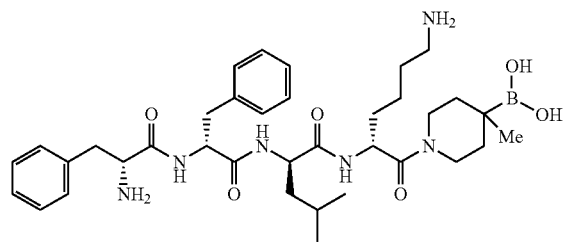
TM-29
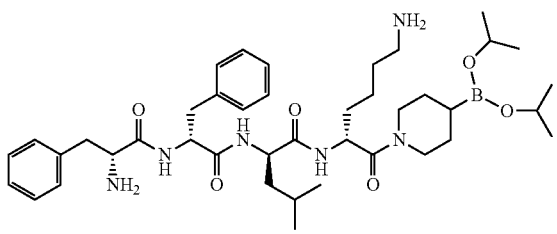
TM-30
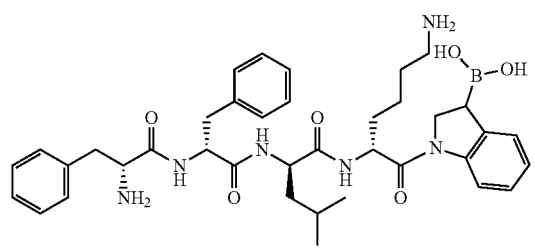
TM-31
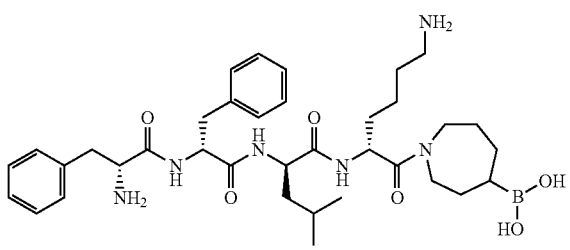
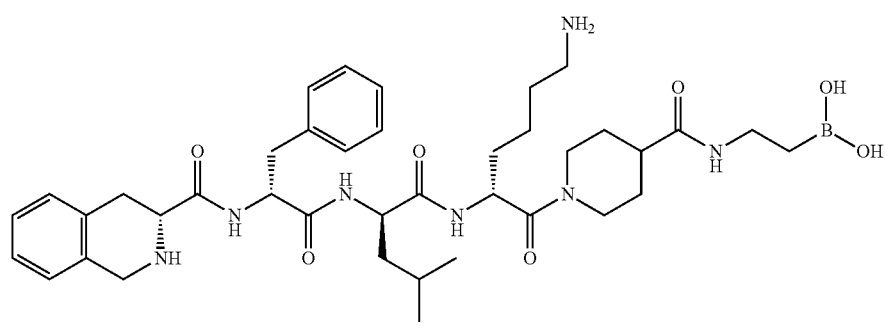
TM-32
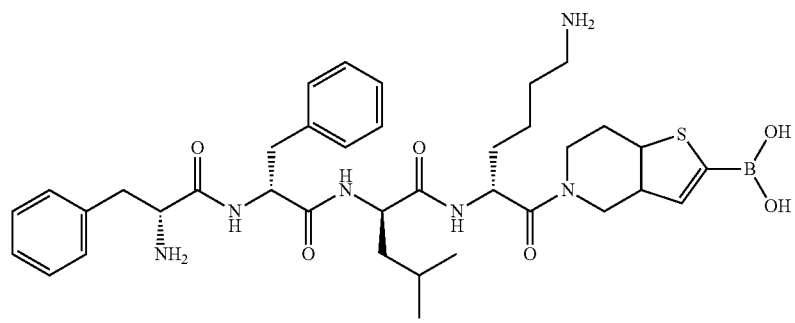
TM-33
TM-34
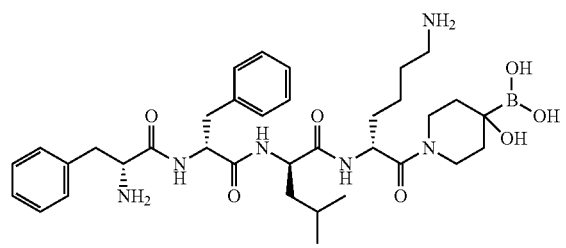
TM-35
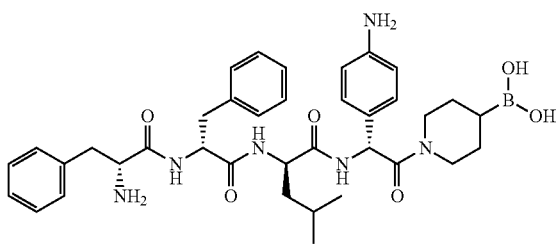

TM-36

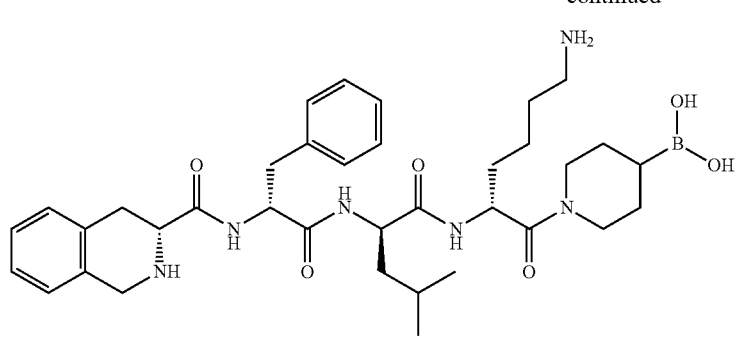

The invention provides a method for preparing the polypeptide compound, the method comprises the following steps:

step 1: preparation of a tetrapeptide intermediate Int-1, wherein the preparation process is as follows:

step 1-1: synthesis of intermediate Int-1-1: swelling 2-CTC Resin using DCM, and then removing solvent to obtain a swelled resin; adding a mixed solution of Fmoc-D-Lys(Boc)-OH and DIEA in DCM to the swelled resin, and performing a reaction at room temperature, and then adding methanol and DIEA to continue the reaction, removing solvent until dryness, and then washing the resulting mixture with DCM to obtain a resin;

step 1-2: synthesis of intermediate Int-1-2: adding piperidine/DMF to the resin obtained in step 1-1, performing a reaction at room temperature, adding piperidine/DMF again, performing a reaction at room temperature, and then removing solvent until dryness, and washing the resulting mixture with DMF; adding Fmoc-D-Leu-OH, HOBT and HBTU respectively to DMF under ice bath conditions for activation, and then adding DIEA, and performing a reaction to obtain an activation solution; and finally adding the activation solution to the resin, and performing a reaction at room temperature, and treating the resin with 5% ninhydrin solution until the color didn't change; removing solvent from the resin and washing with DMF, and removing solvent to obtain an intermediate Int-1-2;

step 1-3: synthesis of intermediate Int-1-3: repeating step 1-2 using the intermediate Int-1-2 obtained in step 1-2;

step 1-4: synthesis of intermediate Int-1-4: repeating step 1-2 using the intermediate Int-1-3 obtained in step 1-3;

step 1-5: synthesis of intermediate Int-1-5: adding Int-1-4 to trifluoroethanol/DCM at room temperature, performing a reaction, and then preforming suction filtration, washing and concentration in sequence, and adding the concentrated solution dropwise to methyl tert-butyl ether with stirring and settling the mixture to obtain tetrapeptide intermediate Int-1;

step 2: preparation of intermediate boric acid pinacol ester: removing a protective group of N-protected boric acid pinacol ester under acidic or alkaline conditions to obtain the boronic acid pinacol ester; wherein the N-protected boric acid pinacol ester can be purchased directly (such as Int-4, Int-5), or can be obtained by one-pot decarboxylated boronation reaction of the corresponding N-protected carboxylic acid (such as Int-2, Int-3);

step 3: preparation of polypeptide compounds:

step 3-1: stirring a solution of Int-1, HOBT, HBTU and DIEA in DCM at room temperature, then adding the boric acid pinacol ester prepared in step 2, and performing a reaction at room temperature, washing, drying, filtering and concentrating the reaction solution to obtain intermediate compound 1-1; and step 3-2: adding an acid (TFA or HCl solution) dropwise to a solution of the intermediate compound 1-1 in DCM, stirring at room temperature, concentrating and purifying the mixture to obtain a polypeptide compound.

The boric acid pinacol ester includes Int-2, Int-3, Int-4, and Int-5, and other boric acid pinacol ester.

wherein the preparation methods of the other boronic acid pinacol esters are similar to those of Int-2, Int-3, Int-4 and Int-5.

The invention provides a compound prepared from the polypeptide compound, wherein the compound includes stereoisomers, polymorphs, solvates, metabolites, prodrugs, or pharmaceutically acceptable salts or esters, or boronic acid polymers (cyclic or acyclic boric acid esters formed from intermolecular dimerization or trimerization) of the polypeptide compound.

Pharmaceutically acceptable salts include inorganic or organic acid salts of basic residues of amines, and alkali metal salts or organic salts of acidic residues such as boric acid or carboxylic acid. Inorganic or organic acid salts of basic residues of amines include the following specific examples: a salt of an inorganic acid such as hydrochloride salt, hydrobromide salt, sulfate, hydrogensulfate, sulfamate, borate, carbonate, and hydrogencarbonate, phosphate, hexafluorophosphate and nitrate, and a salt of an organic acid such as formate, acetate, trifluoroacetate, propionate, succinate, adipate, glycolate, stearate, lactate, malate, tartrate, stearate, citrate, ascorbate, pamoate, hydrochloride, oxalate, maleate, hydroxymaleate, tartrate, phenylacetate, glutamate, camphorsulfonate, benzoate, salicylate, sulfamate, 2-acetoxybenzoate, fumarate, toluenesulfonate, methanesulfonate, ethanedisulfonate, oxalate, isethionate, aspartate, cyclohexanoate sulfonate, fimarate. Alkali metal salts or organic salts of acidic residues such as boric acid or carboxylic acid include the following specific examples: aluminum salt, potassium salt, calcium salt, magnesium salt, zinc salt, argininate, choline salt, diethylamine salt, ethanolamine salt, diethanolamine salt, glycinate, lysinate, meglumine salt and tromethamine salt and the like. These salts can be prepared by methods known in the art.

The invention provides a polypeptide compound or a pharmaceutical composition comprising the compound.

The invention provides use of the polypeptide compound in the manufacture of a medicament for treating diseases associated with κ-opioid receptor.

The disease associated with κ-opioid receptor is selected from pain, inflammation, itching, edema, hyponatremia and hypopotassaemia.

The pain is selected from neuropathic pain, somatic pain, visceral pain, skin pain, arthritis pain, nephrolith pain, hysterotrismus, dysmenorrhea, endometriosis, post-surgical pain, pain after medical treatment, headache, toothache, cervical pain, eye pain, otitis pain, chest pain, abdominal pain, low back and leg pain, gout, rheumatism, rheumatoid, cancer pain and pain associated with gastrointestinal dysfunction and the like.

As used herein, "alkyl", when used alone or in combination with other groups, represents a saturated linear or branched group containing 1-12, preferably 1-8, more preferably 1-6 and even more preferably 1-4 carbon atoms, such as methyl, ethyl, n-propyl, isopropyl, n-butyl, sec-butyl, tert-butyl, pentyl, n-pentyl, n-hexyl, isohexyl, n-heptyl, n-octyl, n-decyl, etc.

As used herein, "alkenyl", when used alone or in combination with other groups, represents a linear or branched group containing 2-12, preferably 2-8, more preferably 2-6 and even more preferably 2-4 carbon atoms and an unsaturated double bond, including linear or branched diene, for example: vinyl, allyl, 1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1,3-butadiene, 1,3-pentadiene, 2-methyl-1,3-butadiene, etc.

As used herein, "alkynyl", when used alone or in combination with other groups, a linear or branched group containing 2-12, preferably 2-8, more preferably 2-6 and even more preferably 2-4 carbon atoms and an unsaturated triple bond, for example: ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, linear or branched diynes or triynes, such as 1,3-butadiyne, etc., which may be further substituted with aryl.

As used herein, "cycloalkyl", when used alone or in combination with other groups, represents a 3-7, preferably 3-6, and more preferably 3-5 membered carbocyclic group, such as cyclopropyl, cyclobutyl, cyclopentyl, cyclohexyl, etc.

As used herein, "aryl", when used alone or in combination with other groups, refers to an optionally substituted aromatic carbocyclic group containing 1, 2 or 3 rings, containing 6-14, preferably 6-10 carbon atoms, which are connected by a bond or in a fused way, for example: phenyl, biphenyl, naphthyl, tetrahydronaphthalene, dihydroindene, which can be further substituted by other aryl or aryl-containing substituents.

As used herein, "heterocyclic group", when used alone or in combination with other groups, represents an optionally substituted a 3-7, preferably a 3-6 membered cyclic group containing more than one heteroatom, which is selected from N, S and O. This group includes saturated, partially saturated and aromatic unsaturated heterocyclic groups. Saturated heterocyclic groups are equivalent to the term "heterocycloalkyl" herein, when used alone or in combination with other groups, include the following examples: aziridinyl, azetidinyl, tetrahydrofuranyl, tetrahydrothienyl, oxazolidinyl, thiazolidinyl, benzothiazolyl, pyrrolidinyl, imidazolidinyl, piperidinyl, piperazinyl, thiazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazapinyl, oxapinyl, thiapinyl, etc., 1-3-oxanyl, etc. The partially saturated heterocyclic group is equivalent to the term "heterocyclenyl" herein, when used alone or in combination with other groups, includes the following examples: dihydrothienyl, dihydropyranyl, dihydrofuranyl, dihydrothiazolyl, etc. The aromatic unsaturated heterocyclic group is equivalent to the term "heteroaryl" herein, when used alone or in combination with other groups, can be a monocyclic ring, and can also be a bonded or fused polycyclic ring, which includes the following examples: thiazolyl, oxazolyl, imidazolyl, isoxazolyl, pyrrolyl, pyrazolyl, triazolyl, tetrazolyl, thienyl, furyl, pyridyl, pyrimidinyl, pyrazinyl, pyridazinyl, indolyl, quinolinyl, isoquinolinyl, quinoxalinyl, bipyridyl, acridinyl, phenanthridinyl, phenanthrolinyl, quinazolonyl, benzimidazolyl, benzofuranyl, benzothienyl, benzothiazolyl, benzoxazolyl, benzisoxazolyl, bipyridyl, biphenylpyridyl.

Herein, unless otherwise specified, "heteroalkyl" and "heterocyclic group" contain one or more heteroatoms, preferably 1-6, more preferably 1, 2, or 3. When the groups contain multiple heteroatoms, the multiple heteroatoms may be the same or different.

"Halogen", when used alone or in combination with other groups, such as forming "haloalkyl", "perhaloalkyl", etc., refers to fluorine, chlorine, bromine or iodine. The term "haloalkyl" represents alkyl as defined above substituted by one or more halogens, including perhaloalkyl, such as fluoromethyl, difluoromethyl, trifluoromethyl, fluoroethyl, difluoroethyl, trifluoromethyl, etc. The term "haloalkoxy" represents haloalkyl as defined above, which is directly connected to an oxygen atom, such as fluoromethoxy, chloromethoxy, fluoroethoxy, chloroethoxy, etc.

"Acyl", when used alone or in combination with other groups, includes the following forms: —C(=O)H, —C(=O)-alkyl, —C(=O)-aryl, —C(=O)-aralkyl and —C(=O)-heteroaryl, such as formyl, acetyl, propionyl, butyryl, isobutyryl, valeryl, hexanoyl, heptanoyl, benzoyl, etc. The non-C(=O)— part in the acyl may be substituted with optional substituents, including but not limited to halogen, lower alkyl (C1-C4 alkyl), aryl or aryl-containing substituents.

"Ester group", when used alone or in combination with other groups, it represents the —COO— group, including: alkoxycarbonyl, such as methoxycarbonyl, ethoxycarbonyl, etc.; aryloxycarbonyl, such as phenoxycarbonyl, naphthoxycarbonyl, etc.; aralkyloxycarbonyl, such as benzyloxycarbonyl, phenethoxycarbonyl, naphthylmethoxycarbonyl; heterocyclyloxycarbonyl, wherein heterocyclyl is defined as above; the non-COO— part of the ester group may be further substituted with optional substituents.

As used herein, a compound or chemical moiety being described with "substituted" means that at least one hydrogen atom of the compound or chemical moiety is replaced by a second chemical moiety. Non-limiting examples of substituents are those present in the exemplary compounds and embodiments as disclosed herein, deuterium, fluorine, chlorine, bromine, iodine; hydroxyl, oxo; amino (primary, secondary, tertiary), imino, nitro, nitroso; cyano, isocyano, alkyl, heteroalkyl, cycloalkyl, heterocycloalkyl, aryl, heteroaryl, alkenyl, cycloalkenyl, alkynyl; lower alkoxy, aryloxy; mercapto, thioether; phosphine; carboxyl, sulfonato, phosphono; acyl, thiocarbonyl, sulfonyl; amide, sulfonamide; ketone; aldehyde; ester, sulfonate; haloalkyl (for example, difluoromethyl, trifluoromethyl); monocyclic or fused or non-fused polycyclic carbocycloalkyl (for example, cyclopropyl, cyclobutyl, cyclopentyl or cyclohexyl); or monocyclic or fused or non-fused polycyclic heterocycloalkyl (for example, pyrrolidinyl, piperidinyl, piperazinyl, morpholinyl or thiazinyl); or a monocyclic or fused or non-fused polycyclic carbocyclic or heterocyclic aryl (e.g., phenyl, naphthyl, thiazolyl, oxazolyl, imidazolyl, isoxazolyl, pyrrolyl, pyrazolyl, triazolyl, tetrazolyl, thienyl, furyl, pyridyl, pyrimidinyl, pyrazinyl, pyridazinyl, indolyl, quinolinyl, isoquinolinyl, quinoxalinyl, bipyridyl, acridinyl, phenanthridinyl, phenanthrolinyl, quinazolonyl, benzimidazolyl, benzofuranyl, benzothienyl, benzothiazolyl, benzoxazolyl, benzisoxazolyl); or aryl-lower alkyl; —CHO; —CO (alkyl); —CO (aryl); —CO$_2$ (alkyl); —CO$_2$ (aryl); —CONH$_2$; —SO$_2$NH$_2$; —OCH$_2$CONH$_2$; —OCHF$_2$; —OCF$_3$; —CF$_3$; —NH$_2$; —NH(alkyl); —N(alkyl)$_2$; —NH(aryl); —N(alkyl)(aryl); —N(aryl)$_2$. In addition, when the substituent is oxygen, it means that two hydrogen atoms on the same or different carbons are substituted by the same oxygen atom to form a carbonyl or cyclic ether, such as ketone carbonyl, aldehyde carbonyl, ester carbonyl, amide carbonyl, ethylene oxide, etc. In addition, these parts can also be optionally substituted by fused ring structures or bridges (for example, —OCH$_2$O—). In the present invention, they can preferably be substituted by one, two, three, four, five or six substituents which are independently selected from halogen, alkyl, alkoxy, aryl, aryloxy, and —N(aryl)$_2$, or substituted by perhalogen, such as trifluoromethyl, perfluorophenyl. When the substituents contain hydrogen, these substituents may be optionally further substituted by substituents selected from such groups.

Compared with the prior art, the present invention has the following advantages and beneficial effects:

The polypeptide compounds of the present invention are novel polypeptide derivatives containing boric acid structural fragments, wherein boron-containing compounds have delicate characteristics, which can reversibly interact with protein targets. Using polypeptide derivatives obtained by combining boric acid groups with polypeptides as a κ-opioid receptor agonist drug has better analgesic activity.

DETAILED DESCRIPTION

In order to make the objectives, technical solutions and advantages of the present invention clearer, the present invention will be further described in detail below in conjunction with examples. The exemplary embodiments and descriptions of the present invention are only used to explain the present invention and are not intended to limit the present invention.

Example 1

Preparation of Polypeptide Compound TM-1

Step 3-1: A solution of Int-1 (0.545 g, 0.622 mmol), HOBT (0.201 g, 1.492 mmol), HBTU (0.566 g, 1.492 mmol), and DIEA (0.320 g, 2.488 mmol) in DCM (15 mL) were stirred at room temperature for 0.5 h, and then crude Int-4 was added. The mixture was reacted at room temperature for 2 h. The reaction solution was washed with saturated ammonium chloride solution, water and saturated brine, and dried over anhydrous sodium sulfate. After filtration and concentration, the crude product was purified by Prep-HPLC to obtain an intermediate compound 1-1;

Step 3-2: TFA (1 mL) was added dropwise to a solution of 1-1 (500 mg) in DCM (2 mL), and the mixture was stirred at room temperature for 1 h. After concentrating and drying, the crude product was purified by Prep-HPLC to obtain a trifluoroacetate salt of polypeptide compound TM-1.

The mass spectrum and nuclear magnetic resonance characterization of the prepared TM-1 are as follows:

ESI-MS (m/z): 665.4 (M+H+)

1H NMR (400 MHz, DMSO-d6+D2O): δ 7.28-7.21 (m, 10H), 4.70-4.59 (m, 2H), 4.42-4.36 (m, 1H), 4.18-4.11 (m, 1H), 3.98 (s, 1H), 3.13-2.87 (m, 4H), 2.86-2.59 (m, 4H), 1.74-1.09 (m, 14H), 1.00-0.91 (m, 1H), 0.89-0.84 (m, 6H).

The preparation process of Int-1 is as follows:

Step 1-1: Synthesis of Intermediate Int-1-1: 2-CTC Resin (degree of substitution was 0.993 mmol/g, 2.000 g) was swelled using DCM (20 mL) at room temperature for 15 min, and the solvent was removed. The mixed solution of Fmoc-D-Lys(Boc)-OH (1.120 g, 2.4 mmol) and DIEA (0.516 g, 4.0 mmol) in DCM (15 mL) was added to the swollen resin and the mixture was reacted at room temperature for 2 h; then methanol (2 mL) and DIEA (1 mL) were added to continue the reaction for 0.5 h. The solvent was removed until dryness and the resulting mixture was washed with DCM (30 mL) for three times, and finally washed with DMF (30 mL) for three times, and after that the resin was directly put into the next reaction;

Step 1-2: Piperidine/DMF (V/V=1/4, 20 mL) was added to the product obtained in step 1-1, and the mixture was reacted for 10 min at room temperature, and then removed of solvent until dryness. Piperidine/DMF (V/V=1/4, 20 mL) was added again, and the mixture was reacted for 10 min at room temperature, and then removed of solvent until dryness, and washed with DMF (30 mL) for 5 times. After the last washing, the pH of the waste liquid was tested to be neutral; Fmoc-D-Leu-OH (1.809 g, 4.0 mmol), HOBT (0.543 g, 4.0 mmol) and HBTU (1.521 g, 4.0 mmol) were added to DMF (20 mL) under ice bath conditions for activation for 10 min, and then DIEA (0.780 g, 6 mmol) was added and the mixture was reacted for 5 min. Finally, the activation solution was added to the resin and the mixture was reacted at room temperature for 2 h. The resin was treated with 5% ninhydrin solution (heated at 100° C. for 10 min) and the color did not change. The solution was removed until dryness and washed with DMF (30 mL) for 5 times. After the last washing, the pH of the waste liquid was tested to be neutral. After removing solvent until dryness, the resulting mixture was directly used in the next reaction;

Step 1-3: Piperidine/DMF (V/V=1/4, 20 mL) was added to the product obtained in step 1-2, and the mixture was reacted for 10 min at room temperature, and then removed of solvent until dryness. Piperidine/DMF (V/V=1/4, 20 mL) was added again, and the mixture was reacted for 10 min at room temperature, and then removed of solvent until dryness, and washed with DMF (30 mL) for 5 times. After the last washing, the pH of the waste liquid was tested to be neutral; Fmoc-D-Phe-OH (1.547 g, 4.0 mmol), HOBT (0.543 g, 4.0 mmol) and HBTU (1.521 g, 4.0 mmol) were added to DMF (20 mL) under ice bath conditions for activation for 10 min, and then DIEA (0.780 g, 6 mmol) was added and the mixture was reacted for 5 min. Finally, the activation solution was added to the resin and the mixture was reacted at room temperature for 2 h. The resin was treated with 5% ninhydrin solution (heated at 100° C. for 10 min) and the color did not change. The solution was removed until dryness and washed with DMF (30 mL) for 5 times. After the last washing, the pH of the waste liquid was tested to be neutral. After removing solvent until dryness, the resulting mixture was directly used in the next reaction;

Step 1-4: Synthesis of Intermediate Int-1-4: Piperidine/DMF (V/V=1/4, 20 mL) was added to the product obtained in step 1-3, and the mixture was reacted for 10 min at room temperature, and then removed of solvent until dryness. Piperidine/DMF (V/V=1/4, 20 mL) was added again, and the mixture was reacted for 10 min at room temperature, and then removed of solvent until dryness, and washed with DMF (30 mL) for 5 times. After the last washing, the pH of the waste liquid was tested to be neutral; Boc-D-Phe-OH (1.547 g, 4.0 mmol), HOBT (0.543 g, 4.0 mmol) and HBTU (1.521 g, 4.0 mmol) were added to DMF (20 mL) under ice bath conditions for activation for 10 min, and then DIEA (0.780 g, 6 mmol) was added and the mixture was reacted for 5 min. Finally, the activation solution was added to the resin and the mixture was reacted at room temperature for 2 h. The resin was treated with 5% ninhydrin solution (heated at 100° C. for 10 min) and the color did not change. The solution was removed until dryness and washed with DMF (30 mL) for 5 times. After the last washing, the pH of the waste liquid was tested to be neutral. After removing solvent until dryness, the resulting mixture was directly used in the next reaction;

Step 1-5: Int-1-4 (4.2 g) was added to trifluoroethanol/DCM (50 mL, V=/V=1/4) at room temperature, and the mixture was reacted for 2 h at room temperature. The resulting mixture was filtered with suction, and washed twice with DCM (30 mL), and the organic phase was concentrated to about 5 mL. The concentrated solution was added dropwise to 100 mL of methyl tert-butyl ether with stirring and the mixture was settled to obtain 2.10 g of product, which was detected by LCMS as target product Int-1.

ESI-MS (m/z): 754.4 (M+H$^+$)

The preparation process of Int-4 is as follows:
TFA (1 mL) was added dropwise to a solution of 1-N-tert-butoxycarbonylpiperidine-4-boronic acid pinacol ester (0.045 g, 1.1 eq) in DCM (2 mL), and the mixture was stirred at room temperature for 0.5 h. The mixture was concentrated to dryness under reduced pressure, and the obtained transparent oil was directly used for the next reaction.

ESI-MS (m/z): 212.3 (M+H$^+$)

Example 2

Preparation of Polypeptide Compound TM-2

This example was based on example 1 except that:
The amount of Int-1 was 0.093 g; Int-4 was replaced with pyrrole-3-boronic acid pinacol ester; the synthesis of pyrrole-3-boronic acid pinacol ester was similar to Int-4, and was achieved by removing the protective group of N-tert-butoxycarbonyl-pyrrole-3-boronic acid pinacol ester under acidic conditions. The obtained crude product was purified by Prep-HPLC to obtain two isomers of the trifluoroacetate salt of the target compound TM-2, TM-2A (10.5 mg) and TM-2B (12.2 mg). The structures were identified as (R)-1-(D-Phe-D-Phe-D-Leu-D-Lys)-3-pyrrolidineboronic acid and (S)-1-(D-Phe-D-Phe-D-Leu-D-Lys)-3-pyrrolidineboronic acid, respectively.

The mass spectrum and nuclear magnetic resonance characterization of the prepared TM-2A were as follows:
ESI-MS (m/z): 651.4 (M+H$^+$)
1H NMR (400 MHz, DMSO): δ8.76-8.73 (m, 1H), 8.38-8.16 (m, 2H), 8.02 (s, 3H), 7.70 (s, 3H), 7.39-7.13 (m, 10H), 4.69-4.64 (m, 1H), 4.52-4.43 (m, 2H), 4.02 (s, 1H), 3.44-3.25 (m, 3H), 3.14-3.02 (m, 3H), 2.96-2.90 (m, 1H), 2.87-2.66 (m, 3H), 2.01-1.92 (m, 1H), 1.71-1.29 (m, 11H), 0.92-0.87 (m, 6H).

The mass spectrum and nuclear magnetic resonance characterization of the prepared TM-2B were as follows:
ESI-MS (m/z): 651.4 (M+H$^+$)
1H NMR (400 MHz, DMSO): δ8.76-8.70 (m, 1H), 8.39-8.21 (m, 2H), 8.03 (s, 3H), 7.70 (s, 3H), 7.41-7.15 (m, 10H), 4.69-4.66 (m, 1H), 4.55-4.44 (m, 2H), 4.05 (s, 1H), 3.48-3.30 (m, 3H), 3.18-3.02 (m, 3H), 3.01-2.90 (m, 1H), 2.92-2.71 (m, 3H), 2.03-1.97 (m, 1H), 1.70-1.20 (m, 11H), 0.90-0.85 (m, 6H).

Example 3

Preparation of Polypeptide Compound TM-3

This example was based on example 1 except that:
The amount of Int-1 was 0.090 g; Int-4 was replaced with 2,5-dihydro-1H-pyrrole-3-boronic acid pinacol ester; the synthesis of 2,5-dihydro-1H-pyrrole-3-boronic acid pinacol ester was similar to Int-4, and was achieved by removing the protective group of N-tert-butoxycarbonyl-2,5-dihydro-1H-pyrrole-3-boronic acid pinacol ester under acidic conditions. The obtained crude product was purified by Prep-HPLC to obtain 13.3 mg of the trifluoroacetate salt of the target compound TM-3.

The mass spectrum and nuclear magnetic resonance characterization of the prepared TM-3 were as follows:
ESI-MS (m/z): 649.4 (M+H$^+$)
1H NMR (400 MHz, CD$_3$OD): δ 7.44-7.12 (m, 10H), 6.58-6.34 (m, 1H), 4.77-4.52 (m, 3H), 4.48-4.25 (m, 4H), 4.11-4.06 (m, 1H), 3.28-3.18 (m, 1H), 3.06-2.89 (m, 4H), 1.88-1.80 (m, 1H), 1.79-1.38 (m, 8H), 1.02-0.91 (m, 6H).

Example 4

Preparation of Polypeptide Compound TM-4

This example was based on example 1 except that:
The amount of Int-1 was 0.057 g; Int-4 was replaced with aminomethylphenylboronic acid pinacol ester. The amount of aminomethylphenylboronic acid pinacol ester was 18 mg. The obtained crude product was purified by Prep-HPLC to obtain 20.1 mg of the trifluoroacetate salt of the target compound TM-4.

The mass spectrum and nuclear magnetic resonance characterization of the prepared TM-4 were as follows:
ESI-MS (m/z): 687.4 (M+H$^+$)
1H NMR (400 MHz, DMSO): δ 8.77-8.72 (m, 1H), 8.49-8.33 (m, 2H), 8.11-7.95 (m, 5H), 7.66 (d, J=8.8 Hz, 4H), 7.40-7.06 (m, 12H), 4.69-4.64 (m, 1H), 4.49-4.35 (m, 1H), 4.34-4.23 (m, 3H), 4.01 (s, 1H), 3.19-3.03 (m, 2H), 2.98-2.87 (m, 1H), 2.86-2.69 (m, 3H), 1.78-1.45 (m, 7H), 1.36-1.25 (m, 2H), 0.97- 0.74 (m, 6H).

Example 5

Preparation of Polypeptide Compound TM-5

This example was based on example 1 except that:
The amount of Int-1 was 0.075 g; Int-4 was replaced with 3,6-dihydro-2H-pyridine-5-boronic acid pinacol ester; the synthesis of 3,6-dihydro-2H-pyridine-5-boronic acid pinacol ester was similar to Int-4, and was achieved by removing the protective group of N-tert-butoxycarbonyl-3,6-dihydro-2H-pyridine-5-boronic acid pinacol ester under acidic conditions. The obtained crude product was purified by Prep-HPLC to obtain 22.0 mg of the trifluoroacetate salt of the target compound TM-5.

The mass spectrum and nuclear magnetic resonance characterization of the prepared TM-5 were as follows:
ESI-MS (m/z): 663.4 (M+H$^+$)
1H NMR (400 MHz, MeOD): δ 7.52-7.15 (m, 10H), 6.59-6.40 (m, 1H), 4.79-4.64 (m, 1H), 4.42 (dt, J=10.2, 6.1 Hz, 1H), 4.30-3.94 (m, 3H), 3.85-3.53 (m, 2H), 3.32-3.12

(m, 2H), 3.04-2.91 (m, 4H), 2.27 (s, 2H), 1.97-1.55 (m, 7H), 1.54-1.32 (m, 2H), 1.00-0.95 (m, 6H).

Example 6

Preparation of Polypeptide Compound TM-6

This example was based on example 1 except that:
The amount of Int-1 was 0.075 g; Int-4 was replaced with p-aminophenylboronic acid pinacol ester. The amount of p-aminophenylboronic acid pinacol ester was 22 mg. The obtained crude product was purified by Prep-HPLC to obtain 3.0 mg of the trifluoroacetate salt of the target compound TM-6.

The mass spectrum and nuclear magnetic resonance characterization of the prepared TM-6 were as follows:
ESI-MS (m/z): 755.4 (M+H$^+$)
1H NMR (400 MHz, CD$_3$OD): δ 7.79-7.47 (m, 4H), 7.44-7.12 (m, 10H), 4.79-4.66 (m, 1H), 4.58-4.35 (m, 2H), 4.09-4.06 (m, 1H), 3.05-2.90 (m, 4H), 2.09-1.89 (m, 1H), 1.88-1.61 (m, 6H), 1.61-1.45 (m, 2H), 1.41-1.34 (m, 2H), 1.06-0.92 (m, 6H).

Example 7

Preparation of Polypeptide Compound TM-7

This example was based on example 1 except that:
The amount of Int-1 was 0.190 g; Int-4 was replaced with Int-2. The obtained crude product was purified by Prep-HPLC to obtain 33.0 mg of the trifluoroacetate salt of the target compound TM-7.

The mass spectrum and nuclear magnetic resonance characterization of the prepared TM-7 were as follows:
ESI-MS (m/z): 705.4 (M+H$^+$)
1H NMR (400 MHz, DMSO-d6): δ 8.58 (dd, J=160.0, 8.2 Hz, 1H), 8.18-7.84 (m, 3H), 7.69 (s, 2H), 7.43-7.14 (m, 10H), 4.83-4.40 (m, 2H), 4.40-4.20 (m, 1H), 4.19-3.66 (m, 2H), 3.18-3.03 (m, 3H), 2.96-2.60 (m, 5H), 1.87-1.58 (m, 6H), 1.57-1.41 (m, 6H), 1.41-1.22 (m, 10H), 0.92-0.84 (m, 6H).

The preparation process of Int-2 is as follows:
Step 2-2-1: DIC (0.070 g, 0.55 mmol), DMAP (0.006, 0.05 mmol), N-hydroxyphthalimide (0.098 g, 0.6 mmol) were added to a solution of Int-2-1 (0.135 g, 0.5 mmol) in DCM (15 mL) at room temperature and the mixture was stirred at room temperature for 2 h. The reaction solution was diluted with 20 mL DCM and respectively washed with 1N HCl and water twice. The organic phases were combined, dried over anhydrous sodium sulfate, filtered, and concentrated to obtain a white solid Int-2-2 (0.120 g), which was directly used in the next reaction. Int-2-1 was 7-(tert-butoxycarbonyl)-7-azaspiro[3.5]nonane-2-carboxylic acid;

Step 2-2-2: Reaction flask A: Under the protection of nitrogen at 0° C., MeLi (1.6M, 1 mL) was slowly added to a solution of bis(pinacolato)diboron (0.420 g, 1.65 mmol) in anhydrous THF (7 mL). After addition, the mixture was continued to be stirred at 0° C. for 0.5 h, and then at room temperature for 0.5 h.

Reaction flask B: Int-2-2 (0.12 g) and magnesium bromide diethyl ether complex (0.129 g) were dissolved in anhydrous THF (3 mL) under nitrogen protection at 0° C., and then nickel chloride hexahydrate (0.012 g), 4,4'-dimethoxy-2,2'-bipyridine (0.014 g) and anhydrous THF (3 mL) were added with stirring for 0.5 h until the reaction system turned pale green.

The solution in reaction flask A was one-time added to reaction flask B at 0° C., and the reaction system turns brown. The mixture was stirred at 0° C. for 1 h, and then warmed to room temperature and stirred for 1 h. TLC was used to monitor the completion of the Int-2-2 reaction. The reaction mixture was added to 20 mL of saturated ammonium chloride solution, and the mixture was stirred for 10 min. 25 mL of ethyl acetate was added for extraction, and the aqueous phase was extracted with 15 mL of ethyl acetate; the combined organic phase was washed with saturated sodium chloride solution twice, dried over anhydrous sodium sulfate, filtered and concentrated to obtain 0.550 g crude product; the crude product was purified by column chromatography to obtain 0.11 g of transparent oily substance, ESI-MS (m/z): 352.3 (M+H+);

Step 2-2-3: Int-2-3 (0.11 g, 0.313 mmol) was added to DCM (4 mL), and then TFA (2 mL) was added. The mixture was stirred at room temperature for 0.5 h and then concentrated to dryness to obtain crude product oil (Int-2), which was directly used in the next reaction, ESI-MS (m/z): 252.3 (M+H+).

Example 8

Preparation of Polypeptide Compound TM-8

This example was based on example 1 except that:
The amount of Int-1 was 0.220 g; Int-4 was replaced with Int-3. The obtained crude product was purified by Prep-HPLC to obtain 6.5 mg of the trifluoroacetate salt of the target compound TM-8.

The mass spectrum and nuclear magnetic resonance characterization of the prepared TM-8 were as follows:
ESI-MS (m/z): 680.4 (M+H+)
1H NMR (400 MHz, DMSO-d6+D2O): δ 7.41-7.22 (m, 10H), 4.79-4.69 (m, 1H), 4.44-4.42 (m, 1H), 4.11-4.09 (m, 2H), 3.95-3.57 (m, 4H), 2.99-2.92 (m, 4H), 2.20-2.00 (m, 2H), 1.85-1.33 (m, 13H), 1.02-0.96 (m, 6H).

The preparation process of Int-3 is as follows:
Step 2-3-1: DIC (0.3 g, 1.1 eq), DMAP (0.027 g, 0.1 eq), N-hydroxyphthalimide (0.42 g, 1.2 eq) were added to a solution of Int-3-1 (1.0 g, 1 eq) in DCM (15 mL) at room temperature and the mixture was stirred at room temperature for 2 h. The reaction solution was diluted with 20 mL DCM and washed with 1N HCl and water twice, respectively. The organic phases were dried over anhydrous sodium sulfate, filtered, and concentrated to obtain a white solid Int-3-2 (1.29 g), which was directly used in the next reaction. Int-3-1 was 4-(tert-butoxycarbonylamino)-1-fluorenyl-methoxycarbonylpiperidine-4-carboxylic acid;
ESI-MS (m/z): 612.2 (M+H$^+$).

Step 2-3-2: Reaction flask A: Under the protection of nitrogen at 0° C., MeLi (1.6M, 4 ml, 3 eq) was slowly added to a solution of bis(pinacolato)diboron (1.798 g, 3.3 eq) in anhydrous THF (7 mL). After addition, the mixture was continued to be stirred at 0° C. for 0.5 h, and then at room temperature for 0.5 h. Reaction flask B: Int-3-2 (1.29 g) and magnesium bromide diethyl ether complex (0.545 g, 1 eq) were dissolved in anhydrous THF (3 mL) under nitrogen protection at 0° C., and then nickel chloride hexahydrate (0.05 g, 0.1 eq), 4,4'-dimethoxy-2,2'-bipyridine (0.06 g, 0.13 eq) and anhydrous THF (7 mL) were added with stirring for 0.5 h until the reaction system turned pale green.

The solution in reaction flask A was one-time added to reaction flask B at 0° C., and the reaction system turned brown. The mixture was stirred at 0° C. for 1 h, and then warmed to room temperature and stirred for 1 h. TLC was used to monitor the completion of the Int-3-2 reaction. The reaction mixture was added to 50 mL of saturated ammonium chloride solution, and the mixture was stirred for 10 min. 25 mL of ethyl acetate was added for extraction, and the aqueous phase was extracted with 25 mL of ethyl acetate; the combined organic phase was washed with saturated sodium chloride solution twice, dried over anhydrous sodium sulfate, filtered and concentrated to obtain 3.00 g crude product; the crude product was purified by column chromatography to obtain 0.650 g of transparent oily substance, (yield: 55%)

ESI-MS (m/z): 549.3 (M+H$^+$)

Step 2-3-3: Int-3-3 (0.08 g, 0.146 mmol) and methylamine methanol solution (4M, 4 mL) were stirred at room temperature for 0.5 h, and concentrated to dryness under reduced pressure. The crude product oil obtained was Int-3, which was directly used into the next reaction; ESI-MS (m/z): 327.2 (M+H$^+$).

Example 9

Preparation of Polypeptide Compound TM-9

This example was based on example 1 except that: Int-4 was replaced with pyrrole-2-boronic acid pinacol ester. The obtained crude product was purified by Prep-HPLC to obtain two isomers TM-9A (58.1 mg) and TM-9B (60.2 mg) of the trifluoroacetate salt of the target compound TM-9. The structures were identified as (R)-1-(D-Phe-D-Phe-D-Leu-D-Lys)-2-pyrrolidineboronic acid and (S)-1-(D-Phe-D-Phe-D-Leu-D-Lys)-2-pyrrolidineboronic acid.

The mass spectrum and nuclear magnetic resonance characterization of the prepared TM-9A were as follows:

ESI-MS (m/z): 651.5 (M+H$^+$)

1H NMR (400 MHz, DMSO): δ 8.87-8.75 (m, 1H), 8.39-8.16 (m, 2H), 8.05 (s, 3H), 7.72 (s, 3H), 7.41-7.13 (m, 10H), 4.68-4.65 (m, 2H), 4.52-4.40 (m, 1H), 4.08-4.02 (m, 1H), 3.74-3.55 (m, 2H), 3.34-3.22 (m, 2H), 3.06-2.80 (m, 5H), 2.25-1.26 (m, 7H), 0.92-0.87 (m, 6H).

The mass spectrum and nuclear magnetic resonance characterization of the prepared TM-9B were as follows:

ESI-MS (m/z): 651.5 (M+H$^+$)

1H NMR (400 MHz, DMSO): δ 8.88-8.75 (m, 1H), 8.42-8.16 (m, 2H), 8.05 (s, 3H), 7.75 (s, 3H), 7.4-7.10 (m, 10H), 4.69-4.64 (m, 2H), 4.50-4.41 (m, 1H), 4.09-4.03 (m, 1H), 3.75-3.55 (m, 2H), 3.38-3.22 (m, 2H), 3.09-2.80 (m, 5H), 2.20-1.20 (m, 7H), 0.93-0.89 (m, 6H).

Example 10

Preparation of Two Isomers TM-10A and TM-10B of Polypeptide Compound TM-10

Anhydrous magnesium sulfate (10 eq) and pinacol (5 eq) were added to a solution of TM-2A (20 mg) or TM-2B (20 mg) in THF, and the mixture was stirred overnight at room temperature. After filtration and concentration, the crude product was purified by Prep-HPLC to obtain two isomers of the target compound, TM-10A (5.1 mg) and TM-10B (5.7 mg). The structures were identified as (R)-1-(D)-Phe-D-Phe-D-Leu-D-Lys)-3-pyrrolidine borate pinacol ester and (S)-1-(D-Phe-D-Phe-D-Leu-D-Lys)-3-pyrrolidine borate pinacol ester, respectively.

The mass spectrum and nuclear magnetic resonance characterization of the prepared TM-10A were as follows:

ESI-MS (m/z): 733.5 (M+H$^+$)

1H NMR (400 MHz, DMSO): δ8.76-8.73 (m, 1H), 8.38-8.16 (m, 2H), 8.02 (s, 3H), 7.70 (s, 3H), 7.39-7.13 (m, 10H), 4.69-4.64 (m, 1H), 4.52-4.43 (m, 2H), 4.02 (s, 1H), 3.44-3.25 (m, 3H), 3.14-3.02 (m, 3H), 2.96-2.90 (m, 1H), 2.87-2.66 (m, 3H), 2.01-1.92 (m, 1H), 1.71-1.29 (m, 11H), 1.20 (s, 12H), 0.92-0.87 (m, 6H).

The mass spectrum and nuclear magnetic resonance characterization of the prepared TM-10B were as follows:

ESI-MS (m/z): 733.5 (M+H$^+$)

1H NMR (400 MHz, DMSO): δ8.76-8.70 (m, 1H), 8.39-8.21 (m, 2H), 8.03 (s, 3H), 7.70 (s, 3H), 7.41-7.15 (m, 10H), 4.69-4.66 (m, 1H), 4.55-4.44 (m, 2H), 4.05 (s, 1H), 3.48-3.30 (m, 3H), 3.18-3.02 (m, 3H), 3.01-2.90 (m, 1H), 2.92-2.71 (m, 3H), 2.03-1.97 (m, 1H), 1.70-1.20 (m, 11H), 1.20 (s, 12H), 0.90-0.85 (m, 6H).

Example 11

Preparation of Two Isomers TM-11A and TM-11B of Polypeptide Compound TM-11

The method in this example was similar to that of example 10 except that pinacol was replaced with citric acid. After purified by Prep-HPLC, two isomers of the target compound, TM-11A (7.2 mg) and TM-11B (9.1 mg), were obtained, and their structures were identified as (R)-1-(D-Phe-D-Phe-D-Leu-D-Lys)-3-pyrrolidineboronic acid citrate and (S)-1-(D-Phe-D-Phe-D-Leu-D-Lys)-3-pyrrolidineboronic acid citrate, respectively.

The mass spectrum and nuclear magnetic resonance characterization of the prepared TM-11A were as follows:

ESI-MS (m/z): 807.5 (M+H$^+$)

1H NMR (400 MHz, DMSO): δ 13.5 (s, 2H), 8.76-8.73 (m, 1H), 8.38-8.16 (m, 2H), 8.02 (s, 2H), 7.70 (s, 2H), 7.39-7.13 (m, 10H), 4.69-4.64 (m, 1H), 4.52-4.43 (m, 2H), 4.02 (s, 1H), 3.44-3.25 (m, 3H), 3.14-3.02 (m, 3H), 2.96-2.90 (m, 1H), 2.87-2.66 (m, 3H), 2.61 (s, 4H), 2.01-1.92 (m, 1H), 1.71-1.29 (m, 11H), 1.20 (s, 12H), 0.92-0.87 (m, 6H).

The mass spectrum and nuclear magnetic resonance characterization of the prepared TM-11B were as follows:

ESI-MS (m/z): 807.5 (M+H$^+$)

1H NMR (400 MHz, DMSO): δ 13.5 (s, 2H), 8.76-8.70 (m, 1H), 8.39-8.21 (m, 2H), 8.03 (s, 2H), 7.70 (s, 2H), 7.41-7.15 (m, 10H), 4.69-4.66 (m, 1H), 4.55-4.44 (m, 2H), 4.05 (s, 1H), 3.48-3.30 (m, 3H), 3.18-3.02 (m, 3H), 3.01-2.90 (m, 1H), 2.92-2.71 (m, 3H), 2.61 (s, 4H), 2.03-1.97 (m, 1H), 1.70-1.20 (m, 11H), 1.20 (s, 12H), 0.90-0.85 (m, 6H).

Example 12

Preparation of Two Isomers TM-12A and TM-12B of Polypeptide Compound TM-12

This example was based on example 1 except that: Int-4 was replaced with piperidine-3-boronic acid pinacol ester. The obtained crude product was purified by Prep-HPLC to obtain two isomers TM-12A (15.1 mg) and TM-12B (20.2 mg) of the trifluoroacetate salt of the target compound TM-12. The structures were identified as (R)-1-(D-Phe-D-Phe-D-Leu-D-Lys)-3-piperidine boronic acid and (S)-1-(D-Phe-D-Phe-D-Leu-D-Lys)-3-piperidine boronic acid, respectively.

The mass spectrum and nuclear magnetic resonance characterization of the prepared TM-12A were as follows:

ESI-MS (m/z): 665.4 (M+H$^+$)

$^1$H NMR (400 MHz, DMSO-$d_6$+$D_2O$): δ 7.28-7.21 (m, 10H), 4.71-4.59 (m, 2H), 4.45-4.40 (m, 1H), 4.18-4.10 (m,

1H), 4.01-3.90 (m, 1H), 3.13-2.87 (m, 4H), 2.86-2.59 (m, 4H), 1.74-1.11 (m, 13H), 1.02-0.90 (m, 1H), 0.90-0.84 (m, 6H).

The mass spectrum and nuclear magnetic resonance characterization of the prepared TM-12B were as follows:

ESI-MS (m/z): 665.4 (M+H$^+$)

$^1$H NMR (400 MHz, DMSO-d$_6$+D$_2$O): δ 7.33-7.25 (m, 10H), 4.72-4.59 (m, 2H), 4.43-4.36 (m, 1H), 4.19-4.13 (m, 1H), 4.11-3.92 (s, 1H), 3.12-2.87 (m, 4H), 2.80-2.51 (m, 4H), 1.70-1.03 (m, 13H), 1.05-0.90 (m, 1H), 0.88-0.84 (m, 6H).

Example 13

Preparation of Two Isomers TM-13A and TM-13B of Polypeptide Compound TM-13

This example was based on example 1 except that: Int-4 was replaced with piperidine-2-boronic acid pinacol ester. The obtained crude product was purified by Prep-HPLC to obtain two isomers TM-13A (12.2 mg) and TM-13B (10.0 mg) of the trifluoroacetate salt of the target compound TM-13. The structures were identified as (R)-1-(D-Phe-D-Phe-D-Leu-D-Lys)-2-piperidine boronic acid and (S)-1-(D-Phe-D-Phe-D-Leu-D-Lys)-2-piperidine boronic acid, respectively.

The mass spectrum and nuclear magnetic resonance characterization of the prepared TM-13A were as follows:

ESI-MS (m/z): 665.4 (M+H$^+$)

$^1$H NMR (400 MHz, DMSO-d$_6$+D$_2$O): δ 7.32-7.20 (m, 10H), 4.70-4.58 (m, 2H), 4.48-4.42 (m, 1H), 4.18-4.07 (m, 1H), 4.00-3.92 (m, 1H), 3.13-2.83 (m, 4H), 2.89-2.61 (m, 4H), 1.77-1.13 (m, 13H), 1.00-0.81 (m, 1H), 0.90-0.84 (m, 6H).

The mass spectrum and nuclear magnetic resonance characterization of the prepared TM-13B were as follows:

ESI-MS (m/z): 665.4 (M+H$^+$)

$^1$H NMR (400 MHz, DMSO-d$_6$+D$_2$O): δ 7.30-7.20 (m, 10H), 4.72-4.58 (m, 2H), 4.44-4.42 (m, 1H), 4.16-4.05 (m, 1H), 4.01-3.93 (m, 1H), 3.15-2.83 (m, 4H), 2.92-2.60 (m, 4H), 1.78-1.15 (m, 13H), 1.05-0.80 (m, 1H), 0.97-0.85 (m, 6H).

Example 14

Preparation of Polypeptide Compound TM-14

This example was based on example 1 except that: Int-4 was replaced with 1-tert-butoxycarbonyl-3,6-dihydro-2H-pyridine-5-boronic acid pinacol ester. The obtained crude product was purified by Prep-HPLC to obtain 15.0 mg of trifluoroacetate salt of the target compound TM-14.

The mass spectrum and nuclear magnetic resonance characterization of the prepared TM-14 were as follows:

ESI-MS (m/z): 663.4 (M+H$^+$)

1H NMR (400 MHz, d6-DMSO): δ 8.77-8.70 (m, 1H), 8.38-8.29 (m, 1H), 8.20-8.00 (m, 3H), 7.75-7.50 (brs, 4H), 7.25-7.06 (m, 10H), 6.30-6.28 (m, 1H), 4.79-4.60 (m, 2H), 4.47-4.31 (m, 1H), 4.150-3.90 (m, 3H), 3.85-3.53 (m, 2H), 3.22-3.01 (m, 3H), 2.84-2.71 (m, 3H), 2.27-2.15 (m, 2H), 1.67-1.35 (m, 7H), 1.34-1.22 (m, 3H), 0.90-0.77 (m, 6H).

Example 15

Preparation of Polypeptide Compound TM-15

This example was based on example 1 except that: Int-4 was replaced with tert-butyl 4-[(4,4,5,5-tetramethyl-1,3,2-dioxaborolan-2-yl)methylene]piperidine-1-carboxylate. The obtained crude product was purified by Prep-HPLC to obtain 22.6 mg of the trifluoroacetate salt of the target compound TM-15.

The mass spectrum and nuclear magnetic resonance characterization of the prepared TM-15 were as follows:

ESI-MS (m/z): 677.4 (M+H$^+$)

1H NMR (400 MHz, CD3OD): δ 7.40-7.20 (m, 10H), 5.38-5.29 (m, 1H), 4.70-4.60 (m, 1H), 4.15-4.00 (m, 1H), 3.85-3.66 (m, 2H), 3.50-3.28 (m, 3H), 3.25-3.10 (m, 2H), 3.00-2.81 (m, 4H), 2.75-2.25 (m, 4H), 1.90-1.70 (m, 1H), 1.70-1.63 (m, 6H), 1.52-1.31 (m, 2H), 1.30-1.21 (m, 1H), 0.99-0.82 (m, 6H).

Example 16

Preparation of Two Isomers TM-16A and TM-16B of Polypeptide Compound TM-16

The method in this example was similar to that of example 10 except that TM-2A or TM-2B was replaced with TM-12. After filtration and concentration, the crude product was purified by Prep-HPLC to obtain two isomers, TM-16A (8.1 mg) and TM-16B (12.2 mg), respectively. The structures were identified as (R)-1-(D-Phe-D-Phe-D-Leu-D-Lys)-3-piperidine boronic acid pinacol ester and (S)-1-(D-Phe-D-Phe-D-Leu-D-Lys)-3-piperidine boronic acid pinacol ester, respectively.

The mass spectrum and nuclear magnetic resonance characterization of the prepared TM-16A were as follows:

ESI-MS (m/z): 747.4 (M+H$^+$)

$^1$H NMR (400 MHz, DMSO-d$_6$+D$_2$O): δ 7.29-7.21 (m, 10H), 4.71-4.58 (m, 2H), 4.46-4.40 (m, 1H), 4.18-4.12 (m, 1H), 4.01-3.93 (m, 1H), 3.13-2.88 (m, 4H), 2.86-2.61 (m, 4H), 1.77-1.11 (m, 13H), 1.22 (s, 12H), 1.02-0.88 (m, 1H), 0.90-0.84 (m, 6H).

The mass spectrum and nuclear magnetic resonance characterization of the prepared TM-16B were as follows:

ESI-MS (m/z): 747.4 (M+H$^+$)

$^1$H NMR (400 MHz, DMSO-d$_6$+D$_2$O): δ 7.35-7.25 (m, 10H), 4.72-4.59 (m, 2H), 4.43-4.36 (m, 1H), 4.19-4.13 (m, 1H), 4.11-3.92 (s, 1H), 3.13-2.87 (m, 4H), 2.83-2.51 (m, 4H), 1.75-1.03 (m, 13H), 1.21 (s, 12H), 1.05-0.90 (m, 1H), 0.88-0.84 (m, 6H).

Example 17

Preparation of Polypeptide Compound TM-17

The synthesis method of this example made reference to example 10. After filtration and concentration, the crude product was purified by Prep-HPLC to obtain the target product TM-17 (8.1 mg).

The mass spectrum and nuclear magnetic resonance characterization of the prepared TM-17 were as follows:

ESI-MS (m/z): 745.5 (M+H$^+$)

1H NMR (400 MHz, d6-DMSO): δ 8.78-8.60 (m, 1H), 8.48-8.29 (m, 1H), 8.20-8.00 (m, 3H), 7.75-7.52 (brs, 4H), 7.28-7.07 (m, 10H), 6.32-6.28 (m, 1H), 4.82-4.61 (m, 2H), 4.48-4.32 (m, 1H), 4.150-3.92 (m, 3H), 3.86-3.56 (m, 2H), 3.23-3.02 (m, 3H), 2.84-2.75 (m, 3H), 2.32-2.17 (m, 2H), 1.69-1.36 (m, 7H), 1.35-1.22 (m, 3H), 0.92-0.78 (m, 6H).

Example 18

Preparation of Polypeptide Compound TM-18

This example was based on example 7 except that: Int-2-1 was replaced with 1-(tert-butoxycarbonyl)azetidine-3-carboxylic acid. The obtained crude product was purified by Prep-HPLC to obtain 12.1 mg of the trifluoroacetate salt of the target compound TM-18.

The mass spectrum and nuclear magnetic resonance characterization of the prepared TM-18 were as follows:

ESI-MS (m/z): 637.5 (M+H$^+$)

1H NMR (400 MHz, DMSO-d6): δ 8.58 (m, 3H), 8.18-7.86 (m, 3H), 7.72 (s, 3H), 7.53-7.16 (m, 10H), 4.86-4.41 (m, 2H), 4.42-4.25 (m, 1H), 4.21-3.76 (m, 2H), 3.28-3.05 (m, 3H), 2.92-2.62 (m, 5H), 1.89-1.68 (m, 6H), 1.52-1.40 (m, 6H), 1.40-1.20 (m, 10H), 0.91-0.7 (m, 6H).

Example 19

Preparation of Two Isomers TM-19A and TM-19B of Polypeptide Compound TM-19

The synthesis method of this example made reference to example 2 except that the protective amino acid reagent N-tert-butoxycarbonyl-D-phenylalanine in the synthesis of the corresponding polypeptide intermediate was replaced with (S)-2-benzyl-3-N-tert-butoxycarbonylaminopropionic acid. The obtained crude product was purified by Prep-HPLC to obtain the two isomers of trifluoroacetate salt of the target compound TM-19, TM-19A (9.5 mg) and TM-19B (8.0 mg). The structures were identified as (R)-1-((S-2-benzylaminopropionic acid)-D-Phe-D-Leu-D-Lys)-3-pyrrolidineboronic acid and (S)-1-((S-2-benzylaminopropionic acid)-D-Phe-D-Leu-D-Lys)-3-pyrrolidineboronic acid, respectively.

The mass spectrum and nuclear magnetic resonance characterization of the prepared TM-19A were as follows:

ESI-MS (m/z): 665.5 (M+H$^+$)

1H NMR (400 MHz, DMSO): δ 8.86-8.73 (m, 1H), 8.48-8.20 (m, 2H), 8.05 (brs, 3H), 7.80 (s, 3H), 7.38-7.10 (m, 10H), 4.52-4.43 (m, 2H), 4.02 (s, 1H), 3.66-3.60 (m, 2H), 3.44-3.25 (m, 3H), 3.14-3.02 (m, 3H), 2.97-2.90 (m, 1H), 2.88-2.66 (m, 3H), 2.77-2.73 (m, 1H), 2.05-1.92 (m, 1H), 1.70-1.28 (m, 11H), 0.92-0.89 (m, 6H).

The mass spectrum and nuclear magnetic resonance characterization of the prepared TM-19B were as follows:

ESI-MS (m/z): 665.5 (M+H$^+$)

1H NMR (400 MHz, DMSO): δ 8.86-8.76 (m, 1H), 8.49-8.20 (m, 2H), 8.10 (brs, 3H), 7.90 (s, 3H), 7.45-7.01 (m, 10H), 4.53-4.42 (m, 2H), 4.05 (s, 1H), 3.69-3.60 (m, 2H), 3.47-3.25 (m, 3H), 3.11-3.00 (m, 3H), 2.92-2.84 (m, 1H), 2.84-2.66 (m, 3H), 2.79-2.73 (m, 1H), 2.01-1.92 (m, 1H), 1.73-1.29 (m, 11H), 0.91-0.89 (m, 6H).

Example 20

Preparation of Two Isomers TM-20A and TM-20B of Polypeptide Compound TM-20

The synthesis method of this example made reference to example 2 except that the protective amino acid reagent N-tert-butoxycarbonyl-D-phenylalanine in the synthesis of the corresponding polypeptide intermediate was replaced with (R)-N-tert-butoxycarbonyl-N-(2-phenylpropyl)alanine. The obtained crude product was purified by Prep-HPLC to obtain the two isomers of trifluoroacetate salt of the target compound TM-20, TM-20A (21.2 mg) and TM-20B (15.0 mg). The structures were identified as (R)-1-((R-2-phenylpropyl-Gly)-D-Phe-D-Leu-D-Lys)-3-pyrrolidineboronic acid and (S)-1-((R-2-phenylpropyl-Gly)-D-Phe-D-Leu-D-Lys)-3-pyrrolidineboronic acid.

The mass spectrum and nuclear magnetic resonance characterization of the prepared TM-20A were as follows:

ESI-MS (m/z): 679.4 (M+H$^+$)

1H NMR (400 MHz, DMSO): δ 8.86-8.73 (m, 1H), 8.48-8.20 (m, 2H), 8.05 (brs, 3H), 7.80 (s, 3H), 7.38-7.10 (m, 10H), 4.52-4.43 (m, 2H), 4.38-4.16 (m, 2H), 4.02 (s, 1H), 3.66-3.60 (m, 2H), 3.44-3.25 (m, 3H), 3.14-3.02 (m, 3H), 2.97-2.80 (m, 3H), 2.88-2.66 (m, 1H), 2.77-2.73 (m, 1H), 2.05-1.92 (m, 1H), 1.70-1.28 (m, 14H), 0.92-0.89 (m, 6H).

The mass spectrum and nuclear magnetic resonance characterization of the prepared TM-20B were as follows:

ESI-MS (m/z): 679.4 (M+H$^+$)

1H NMR (400 MHz, DMSO): δ 9.06-8.80 (m, 1H), 8.58-8.30 (m, 2H), 8.00 (brs, 3H), 7.90 (brs, 3H), 7.48-7.20 (m, 10H), 4.50-4.45 (m, 2H), 4.39-4.26 (m, 2H), 4.05 (s, 1H), 3.68-3.60 (m, 2H), 3.49-3.22 (m, 3H), 3.17-3.02 (m, 3H), 2.99-2.83 (m, 3H), 2.88-2.60 (m, 1H), 2.81-2.72 (m, 1H), 2.01-1.90 (m, 1H), 1.75-1.28 (m, 14H), 0.96-0.89 (m, 6H).

Example 21

Preparation of Two Isomers TM-21A and TM-21B of Polypeptide Compound TM-21

The synthesis method of this example made reference to example 2 except that the protective amino acid reagent N-fluorenylmethyloxycarbonyl-D-leucine in the synthesis of the corresponding polypeptide intermediate was replaced with N-fluorenylmethyloxycarbonyl-D-norleucine. The obtained crude product was purified by Prep-HPLC to obtain the two isomers of trifluoroacetate salt of the target compound TM-21, TM-21A (7.2 mg) and TM-21B (8.5 mg). The structures were identified as (R)-1-(D-Phe-D-Phe-D-Nle-D-Lys)-3-pyrrolidineboronic acid and (S)-1-(D-Phe-D-Phe-D-Nle-D-Lys)-3-pyrrolidineboronic acid, respectively.

The mass spectrum and nuclear magnetic resonance characterization of the prepared TM-21A were as follows:

ESI-MS (m/z): 651.4 (M+H$^+$)

1H NMR (400 MHz, DMSO): δ 8.86-8.75 (m, 1H), 8.39-8.12 (m, 2H), 8.00 (s, 3H), 7.87 (s, 3H), 7.41-7.13 (m, 10H), 4.72-4.62 (m, 1H), 4.55-4.41 (m, 2H), 4.03 (s, 1H), 3.48-3.22 (m, 3H), 3.19-3.00 (m, 3H), 2.91-2.83 (m, 1H), 2.88-2.67 (m, 3H), 2.00-1.92 (m, 1H), 1.71-1.20 (m, 14H), 0.90-0.89 (m, 3H).

The mass spectrum and nuclear magnetic resonance characterization of the prepared TM-21B were as follows:

ESI-MS (m/z): 651.4 (M+H$^+$)

1H NMR (400 MHz, DMSO): δ 8.86-8.76 (m, 1H), 8.34-8.10 (m, 2H), 8.01 (s, 3H), 7.88 (s, 3H), 7.42-7.10 (m, 10H), 4.73-4.62 (m, 1H), 4.56-4.40 (m, 2H), 4.02 (s, 1H), 3.49-3.22 (m, 3H), 3.23-3.00 (m, 3H), 2.95-2.82 (m, 1H), 2.89-2.61 (m, 3H), 2.01-1.90 (m, 1H), 1.72-1.17 (m, 14H), 0.93-0.86 (m, 3H).

Example 22

Preparation of Two Isomers TM-22A and TM-22B of Polypeptide Compound TM-22

The synthesis method of this example made reference to example 2 except that the protective amino acid reagent Fmoc-D-lysine in the synthesis of the corresponding polypeptide intermediate was replaced with N2-(9-fluorenylmethoxycarbonyl)-N6-butoxycarbonyl-N6-(2-(2-methoxyethoxy)ethyl)-D-lysine (referring to patent WO2018059331). The obtained crude product was purified by Prep-HPLC to obtain the two enantiomers of trifluoroacetate salt of the target compound TM-22, TM-22A (13.9 mg) and TM-22B (17.1 mg). The structures were identified as (R)-1-(N2-D-Phe-D-Phe-D-Leu-N6-(2-(2-methoxyethoxy)ethyl)-D-Lys)-3-pyrrolidineboronic acid and (S)-1-(N2-D-Phe-D-Phe-D-Leu-N6-(2-(2-methoxyethoxy)ethyl)-D-Lys)-3-pyrrolidineboronic acid, respectively.

The mass spectrum and nuclear magnetic resonance characterization of the prepared TM-22A were as follows:

ESI-MS (m/z): 753.5 (M+H$^+$)

1H NMR (400 MHz, DMSO): δ 8.77-8.74 (m, 1H), 8.39-8.16 (m, 2H), 8.03 (brs, 2H), 7.72 (brs, 3H), 7.43-7.13 (m, 10H), 4.67-4.66 (m, 1H), 4.52-4.40 (m, 2H), 4.02 (s, 1H), 3.58-3.35 (m, 9H), 3.30 (s, 3H), 3.14-3.02 (m, 3H), 2.96-2.90 (m, 1H), 2.88-2.66 (m, 5H), 2.01-1.92 (m, 1H), 1.71-1.29 (m, 11H), 0.92-0.87 (m, 6H).

The mass spectrum and nuclear magnetic resonance characterization of the prepared TM-22B were as follows:

ESI-MS (m/z): 753.5 (M+H$^+$)

1H NMR (400 MHz, DMSO): δ 8.81-8.75 (m, 1H), 8.38-8.13 (m, 2H), 8.05 (brs, 2H), 7.70 (brs, 3H), 7.49-7.12 (m, 10H), 4.63-4.61 (m, 1H), 4.57-4.41 (m, 2H), 4.03 (s, 1H), 3.50-3.30 (m, 9H), 3.28 (s, 3H), 3.15-3.02 (m, 3H), 2.94-2.90 (m, 1H), 2.85-2.66 (m, 5H), 2.04-1.92 (m, 1H), 1.71-1.29 (m, 11H), 0.92-0.88 (m, 6H).

Example 23

Preparation of Polypeptide Compound TM-23

This example was based on example 1 except that: Int-4 was replaced with 1H-indazole-5-boronic acid pinacol ester. The obtained crude product was purified by Prep-HPLC to obtain 10.5 mg of the trifluoroacetate salt of the target compound TM-23.

The mass spectrum and nuclear magnetic resonance characterization of the prepared TM-23 were as follows:

ESI-MS (m/z): 698.4 (M+H$^+$)

1H NMR (400 MHz, DMSO): δ 8.70-8.42 (m, 2H), 8.19-8.02 (m, 1H), 7.65 (m, 1H), 7.44-7.03 (m, 12H), 4.68-4.60 (m, 1H), 4.53-4.35 (m, 1H), 4.37-4.23 (m, 3H), 4.05 (s, 1H), 3.18-3.06 (m, 2H), 2.97-2.83 (m, 1H), 2.80-2.60 (m, 3H), 1.79-1.43 (m, 7H), 1.34-1.22 (m, 2H), 0.98-0.74 (m, 6H).

Example 24

Preparation of Polypeptide Compound TM-24

This example was based on example 7 except that: Int-2-1 was replaced with (1S,4R)-7-(tert-butoxycarbonyl)-7-azabicyclo[2.2.1]heptane-2-carboxylic acid. The obtained crude product was purified by Prep-HPLC to obtain 17.7 mg of the trifluoroacetate salt of the target compound TM-24.

The mass spectrum and nuclear magnetic resonance characterization of the prepared TM-24 were as follows:

ESI-MS (m/z): 677.5 (M+H$^+$)

1H NMR (400 MHz, DMSO-d6): δ 8.59 (m, 3H), 8.17-7.80 (m, 3H), 7.71 (s, 3H), 7.55-7.16 (m, 10H), 4.82-4.40 (m, 1H), 4.49-4.24 (m, 1H), 4.20-3.76 (m, 3H), 3.20-3.05 (m, 3H), 2.92-2.61 (m, 5H), 1.95-1.69 (m, 8H), 1.50-1.40 (m, 8H), 1.42-1.20 (m, 10H), 0.93-0.71 (m, 6H).

Example 25

Preparation of Polypeptide Compound TM-25

This example was based on example 1 except that: Int-4 was replaced with 1-amino-4-cyclohexylboronic acid pinacol ester. The obtained crude product was purified by Prep-HPLC to obtain 11.2 mg of the trifluoroacetate salt of the target compound TM-25.

The mass spectrum and nuclear magnetic resonance characterization of the prepared TM-25 were as follows:

ESI-MS (m/z): 679.4 (M+H$^+$)

$^1$H NMR (400 MHz, DMSO-d$_6$+D$_2$O): δ 7.29-7.20 (m, 10H), 4.74-4.58 (m, 2H), 4.45-4.33 (m, 1H), 4.18-4.10 (m, 1H), 3.95 (s, 1H), 3.16-2.86 (m, 1H), 2.86-2.59 (m, 4H), 1.75-1.12 (m, 18H), 1.00-0.90 (m, 1H), 0.90-0.84 (m, 6H).

Example 26

Preparation of Polypeptide Compound TM-26

This example was based on example 1 except that: Int-4 was replaced with 2-aminoethylboronic acid pinacol ester. The obtained crude product was purified by Prep-HPLC to obtain 11.2 mg of the trifluoroacetate salt of the target compound TM-26.

ESI-MS (m/z): 607.4 (M−18+H$^+$)

1H NMR (400 MHz, DMSO) δ 8.79-8.75 (m, 1H), 8.40-8.38 (m, 1H), 8.03 (s, 3H), 7.852-7.73 (m, 4H), 7.61 (s, 2H), 7.32-7.20 (m, 10H), 4.69-4.63 (m, 1H), 4.39-4.32 (m, 1H), 4.20-4.18 (m, 1H), 4.01 (s, 1H), 3.18-3.01 (m, 4H), 2.95-2.90 (m, 1H), 2.86-2.70 (m, 3H), 1.71-1.58 (m, 2H), 1.56-1.43 (m, 5H), 1.31-1.25 (m, 2H), 0.99-0.87 (m, 6H), 0.84-0.79 (m, 2H).

Example 27

Preparation of Polypeptide Compound TM-27

This example was based on example 1 except that: Int-4 was replaced with 3-azabicyclo[3.1.0]hexyl-1-boronic acid pinacol ester (the synthesis of this fragment made reference to Org. Lett. 2017, 19, 9, 2450-2453). The obtained crude product was purified by Prep-HPLC to obtain trifluoroacetate salt of two isomers TM-27A (6.1 mg) and TM-27B (5.0 mg) of the target compound TM-13. The structures were identified as ((R)-1-(D-Phe-D-Phe-D-Leu-D-Lys)-3-azabicyclo[3.1.0]hexylboronic acid and ((S)-1-(D-Phe-D-Phe-D-Leu-D-Lys)-3-azabicyclo[3.1.0]hexylboronic acid, respectively.

The mass spectrum and nuclear magnetic resonance characterization of the prepared TM-27A were as follows:

ESI-MS (m/z): 663.4 (M+H$^+$)

1H NMR (400 MHz, DMSO): δ 8.73-8.75 (m, 1H), 8.39-8.12 (m, 2H), 8.02 (s, 3H), 7.76 (s, 3H), 7.38-7.13 (m, 10H), 4.66-4.60 (m, 1H), 4.52-4.41 (m, 2H), 4.04 (s, 1H), 3.41-3.25 (m, 3H), 3.14-3.00 (m, 3H), 2.98-2.90 (m, 1H), 2.82-2.60 (m, 3H), 2.00-1.92 (m, 1H), 1.70-1.29 (m, 12H), 0.91-0.85 (m, 6H).

The mass spectrum and nuclear magnetic resonance characterization of the prepared TM-27B were as follows:

ESI-MS (m/z): 663.4 (M+H$^+$)

1H NMR (400 MHz, DMSO): δ 8.81-8.72 (m, 1H), 8.38-8.10 (m, 2H), 8.00 (s, 3H), 7.79 (s, 3H), 7.39-7.12 (m, 10H), 4.66-4.61 (m, 1H), 4.52-4.43 (m, 2H), 4.05 (s, 1H), 3.42-3.22 (m, 3H), 3.14-3.01 (m, 3H), 3.01-2.90 (m, 1H), 2.85-2.60 (m, 3H), 2.03-1.91 (m, 1H), 1.77-1.29 (m, 12H), 0.91-0.86 (m, 6H).

Example 28

Preparation of Polypeptide Compound TM-28

This example was based on example 7 except that: Int-2-1 was replaced with 1-tert-butyloxycarbonyl-4-methyl-4-piperidinecarboxylic acid. The obtained crude product was purified by Prep-HPLC to obtain 23.1 mg of the trifluoroacetate salt of the target compound TM-28.

The mass spectrum and nuclear magnetic resonance characterization of the prepared TM-28 were as follows:

ESI-MS (m/z): 679.5 (M+H$^+$)

$^1$H NMR (400 MHz, DMSO-d$_6$+D$_2$O): δ 7.31-7.20 (m, 10H), 4.75-4.59 (m, 2H), 4.46-4.36 (m, 1H), 4.18-4.11 (m, 1H), 3.98 (s, 1H), 3.13-2.87 (m, 4H), 2.86-2.59 (m, 4H), 1.74-1.09 (m, 14H), 1.53 (s, 3H), 0.89-0.84 (m, 6H).

Example 29

Preparation of Polypeptide Compound TM-29

The method in this example was similar to that of example 10 except that TM-2A or TM-2B was replaced with TM-1, and pinacol was replaced with isopropanol. After purified by Prep-HPLC, the trifluoroacetate salt of the target compound TM-29 (9.0 mg) was obtained.

The mass spectrum and nuclear magnetic resonance characterization of the prepared TM-29 were as follows:

ESI-MS (m/z): 749.5 (M+H$^+$)

$^1$H NMR (400 MHz, DMSO-d$_6$+D$_2$O): δ 7.28-7.21 (m, 10H), 4.70-4.59 (m, 2H), 4.42-4.36 (m, 1H), 4.18-4.11 (m, 1H), 3.98 (s, 1H), 3.82-3.77 (m, 2H), 3.13-2.87 (m, 4H), 2.86-2.59 (m, 4H), 1.74-1.09 (m, 14H), 1.00-0.91 (m, 13H), 0.89-0.84 (m, 6H).

Example 30

Preparation of Polypeptide Compound TM-30

This example was based on example 7 except that: Int-2-1 was replaced with 1-(tert-butoxycarbonyl)indoline-3-carboxylic acid. The obtained crude product was purified by Prep-HPLC to obtain trifluoroacetate salt of the two isomers TM-30A (7.2 mg) and TM-30B (9.0 mg) of the target compound TM-30. The structures were identified as (R)-1-(D-Phe-D-Phe-D-Leu-D-Lys)-3-indoline boronic acid and (S)-1-(D-Phe-D-Phe-D-Leu-D-Lys)-3-indoline boronic acid.

The mass spectrum and nuclear magnetic resonance characterization of the prepared TM-30A were as follows:

ESI-MS (m/z): 699.4 (M+H$^+$)

1H NMR (400 MHz, DMSO+D$_2$O): δ 7.67-7.00 (m, 14H), 4.69-4.64 (m, 1H), 4.49-4.35 (m, 1H), 4.34-4.23 (m, 3H), 4.01 (s, 1H), 2.98-2.87 (m, 1H), 2.86-2.69 (m, 3H), 2.39-2.23 (m, 2H), 1.78-1.45 (m, 7H), 1.36-1.25 (m, 3H), 0.97-0.74 (m, 6H).

The mass spectrum and nuclear magnetic resonance characterization of the prepared TM-30B were as follows:

ESI-MS (m/z): 699.4 (M+H$^+$)

1H NMR (400 MHz, DMSO+D$_2$O): δ 7.67-7.03 (m, 14H), 4.70-4.65 (m, 1H), 4.49-4.33 (m, 1H), 4.34-4.20 (m, 3H), 4.00 (s, 1H), 2.99-2.81 (m, 1H), 2.86-2.68 (m, 3H), 2.34-2.20 (m, 2H), 1.80-1.40 (m, 7H), 1.36-1.25 (m, 3H), 0.99-0.75 (m, 6H).

Example 31

Preparation of Polypeptide Compound TM-31

This example was based on example 7 except that: Int-2-1 was replaced with 1-tert-butoxycarbonyl-azepane-4-carboxylic acid. The obtained crude product was purified by Prep-HPLC to obtain trifluoroacetate salt of the two isomers TM-31A (18.8 mg) and TM-31B (12.0 mg) of the target compound TM-31. The structures were identified as (R)-1-(D-Phe-D-Phe-D-Leu-D-Lys)-4-azacycloheptylboronic acid and (S)-1-(D-Phe-D-Phe-D-Leu-D-Lys)-4-azacycloheptylboronic acid.

The mass spectrum and nuclear magnetic resonance characterization of the prepared TM-31A were as follows:

ESI-MS (m/z): 679.5 (M+H$^+$)

$^1$H NMR (400 MHz, DMSO-d$_6$+D$_2$O): δ 7.32-7.21 (m, 10H), 4.80-4.55 (m, 2H), 4.40-4.36 (m, 1H), 4.18-4.10 (m, 1H), 3.92 (s, 1H), 3.23-2.67 (m, 4H), 2.76-2.58 (m, 4H), 1.79-1.02 (m, 16H), 1.00-0.90 (m, 1H), 0.88-0.84 (m, 6H).

The mass spectrum and nuclear magnetic resonance characterization of the prepared TM-31B were as follows:

ESI-MS (m/z): 679.5 (M+H$^+$)

$^1$H NMR (400 MHz, DMSO-d$_6$+D$_2$O): δ 7.33-7.22 (m, 10H), 4.84-4.50 (m, 2H), 4.41-4.36 (m, 1H), 4.21-4.12 (m, 1H), 3.93 (s, 1H), 3.26-2.67 (m, 4H), 2.72-2.58 (m, 4H), 1.78-1.00 (m, 16H), 1.07-0.91 (m, 1H), 0.89-0.85 (m, 6H).

Example 32

Preparation of Polypeptide Compound TM-32

This example was based on example 1 except that: Int-4 was replaced with Int-5. The obtained crude product was purified by Prep-HPLC to obtain 22.3 mg of trifluoroacetate salt of the target compound TM-32.

The mass spectrum and nuclear magnetic resonance characterization of the prepared TM-32 were as follows:

ESI-MS (m/z): 768.5 (M+H$^+$)

1H NMR (400 MHz, DMSO-d6+D2O): δ 7.29-7.18 (m, 10H), 4.70-4.57 (m, 2H), 4.40-4.33 (m, 1H), 4.22-4.10 (m, 1H), 3.95 (s, 1H), 3.20-2.85 (m, 6H), 2.86-2.44 (m, 5H), 1.74-1.09 (m, 14H), 1.10-0.93 (m, 2H), 0.87-0.80 (m, 6H).

Among them, the preparation process of Int-5 was as follows:

A solution of Int-5-1, HATU and DIEA in DMF was stirred at room temperature for 30 minutes, and then 2-aminoethylboronic acid pinacol ester was added. The mixture was reacted at room temperature for 30 minutes, and then the reaction solution was poured into water, and ethyl acetate was added to extract the solution for three times. The organic phase was dried with anhydrous sodium sulfate, filtered and concentrated to obtain the intermediate compound Int-5-2;

ESI-MS (m/z): 383.3 (M+H+)

TFA was added dropwise to the solution of Int-5-2 in DCM and the mixture was stirred at room temperature for 30 minutes. The mixture was concentrated to dryness under reduced pressure, and the target compound Int-5 was obtained as a transparent oil, which was directly used in the next reaction.

ESI-MS (m/z): 283.3 (M+H+)

Example 33

Preparation of Polypeptide Compound TM-33

This example was based on example 7 except that: Int-2-1 was replaced with 5-tert-butoxycarbonyl-4,5,6,7-tetrahydrothieno[3,2-c]pyridine-2-carboxylic acid. The obtained crude product was purified by Prep-HPLC to obtain 22.1 mg of trifluoroacetate salt of the target compound TM-33.

The mass spectrum and nuclear magnetic resonance characterization of the prepared TM-33 were as follows:

ESI-MS (m/z): 719.4 (M+H$^+$)

$^1$H NMR (400 MHz, DMSO-d$_6$+D$_2$O): δ 7.32-7.11 (m, 11H), 4.80-4.55 (m, 4H), 4.40-4.36 (m, 1H), 4.18-4.10 (m, 1H), 3.92 (s, 1H), 3.23-2.67 (m, 6H), 2.76-2.58 (m, 4H), 1.79-1.02 (m, 12H), 0.88-0.84 (m, 6H).

Example 34

Preparation of Polypeptide Compound TM-34

This example was based on example 7 except that: Int-2-1 was replaced with 1-tert-butoxycarbonyl-4-hydroxy-4-carboxypiperidine. The obtained crude product was purified by Prep-HPLC to obtain 9.5 mg of trifluoroacetate salt of the target compound TM-34.

The mass spectrum and nuclear magnetic resonance characterization of the prepared TM-34 were as follows:

ESI-MS (m/z): 681.4 (M+H$^+$)

1H NMR (400 MHz, DMSO-d6+D2O): δ7.45-7.22 (m, 10H), 4.72-4.61 (m, 1H), 4.47-4.42 (m, 1H), 4.12-4.06 (m, 2H), 3.99-3.59 (m, 4H), 2.97-2.91 (m, 4H), 2.22-2.06 (m, 2H), 1.83-1.30 (m, 13H), 1.00-0.96 (m, 6H).

Example 35

Preparation of Polypeptide Compound TM-35

The synthesis method of this example made reference to example 1 except that the protective amino acid reagent N-tert-butoxycarbonyl-D-lysine in the synthesis of the corresponding polypeptide intermediate was replaced with N-fluorenylmethoxycarbonyl-R-4-tert-butoxycarbonylaminophenylglycine. The obtained crude product was purified by Prep-HPLC to obtain trifluoroacetate salt of the target compound TM-35 (10.2 mg).

The mass spectrum and nuclear magnetic resonance characterization of the prepared TM-35 were as follows:

ESI-MS (m/z): 685.4 (M+H$^+$)

1H NMR (400 MHz, DMSO-d6+D2O): δ7.29-7.21 (m, 14H), 4.77-4.58 (m, 2H), 4.46-4.32 (m, 1H), 4.19-4.12 (m, 1H), 3.99 (s, 1H), 3.12-2.87 (m, 2H), 2.82-2.56 (m, 4H), 1.74-1.09 (m, 8H), 1.01-0.92 (m, 1H), 0.86-0.80 (m, 6H).

Example 36

Preparation of Polypeptide Compound TM-36

The synthesis method of this example made reference to example 1 except that the protective amino acid reagent N-tert-butoxycarbonyl-D-phenylalanine in the synthesis of the corresponding polypeptide intermediate was replaced with N-tert-butoxycarbonyl-D-1,2,3,4-tetrahydroisoquinoline-3-carboxylic acid. The obtained crude product was purified by Prep-HPLC to obtain trifluoroacetate salt of the target compound TM-36 (13.5 mg).

ESI-MS (m/z): 697.3 (M+H+)

1H NMR (400 MHz, DMSO-d6+D2O): δ7.30-7.23 (m, 9H), 4.73-4.57 (m, 2H), 4.46-4.39 (m, 1H), 4.22-4.10 (m, 3H), 3.95 (s, 1H), 3.10-2.86 (m, 4H), 2.80-2.54 (m, 4H), 1.74-1.05 (m, 14H), 1.00-0.92 (m, 1H), 0.87-0.81 (m, 6H).

The solvent used for swelling CTC resin, the solvent used for washing the resin and the solvent used in the condensation condition in the present invention include but not limited to one or more solvents selected from DCM, THF, DMF, DMA, NMP, DMSO; the amino acid protecting group and side chain protecting group, in addition to fluorenylmethoxycarbonyl and tert-butoxycarbonyl, includes benzyloxycarbonyl, methoxycarbonyl, ethoxycarbonyl, trifluoroacetyl, p-methoxybenzyl, allyloxycarbonyl and the like; the condensation agent includes but not limited to HATU, HBTU, HCTU, EDCI, PyBOP, CDI, HOBT and the like.

The preparation process of the tetrapeptide intermediate Int-1 was as follows:

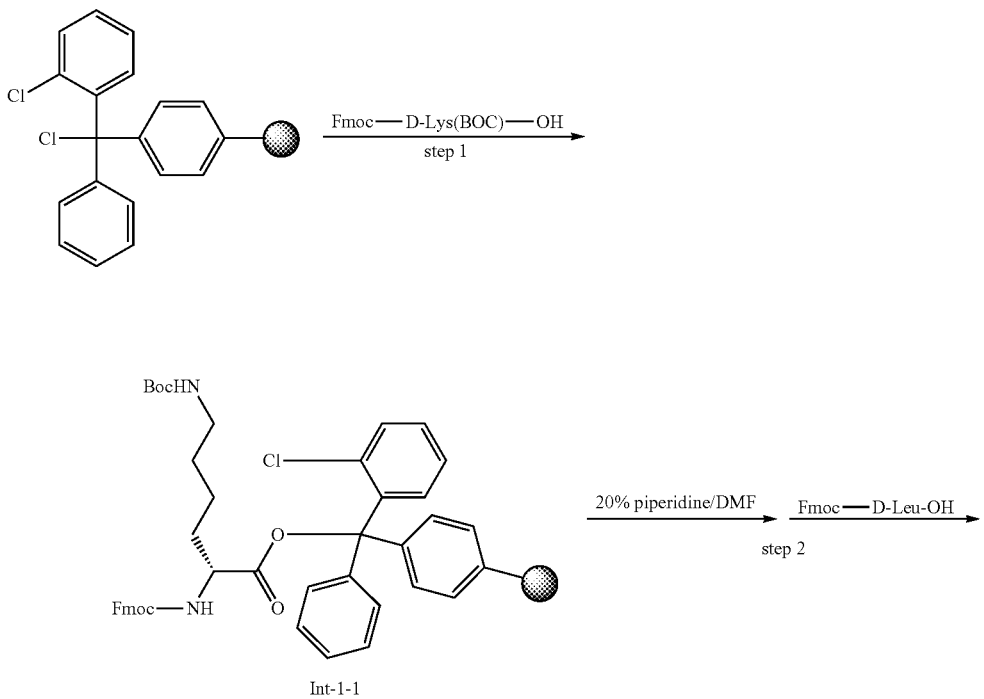

-continued
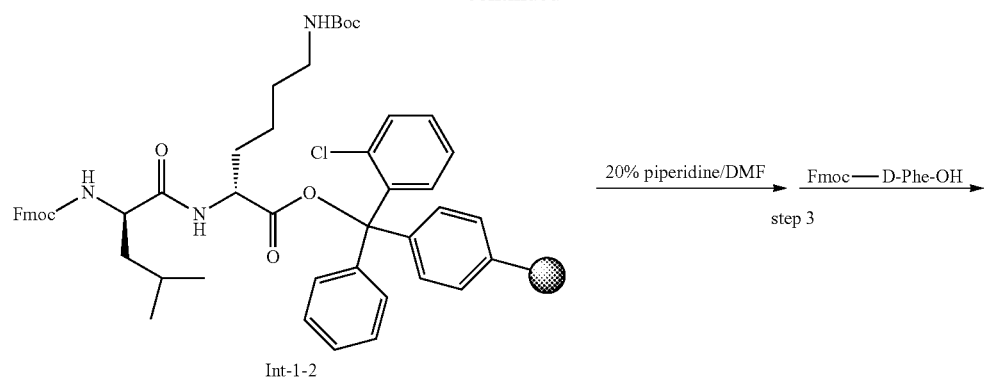
Int-1-2
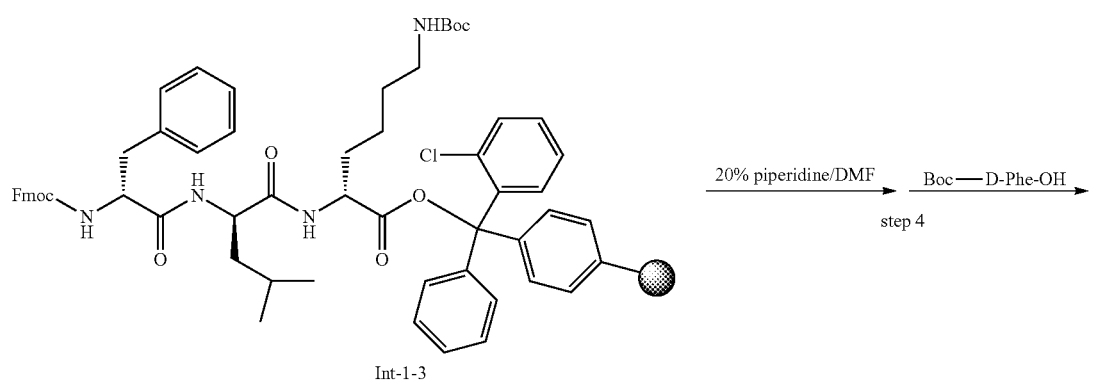
Int-1-3
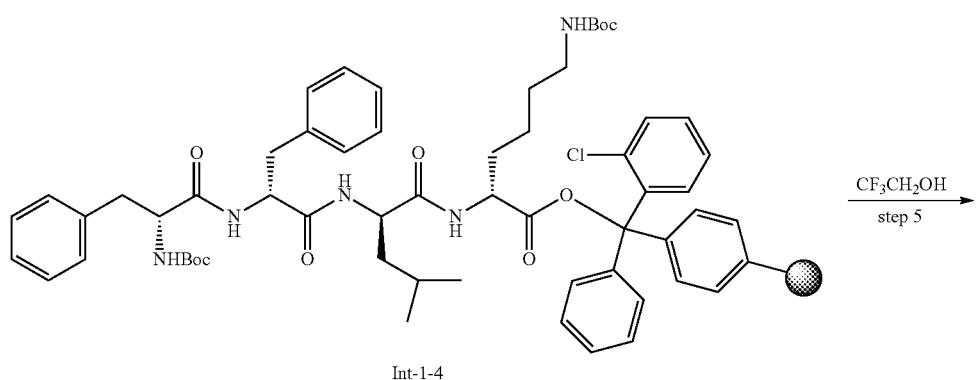
Int-1-4
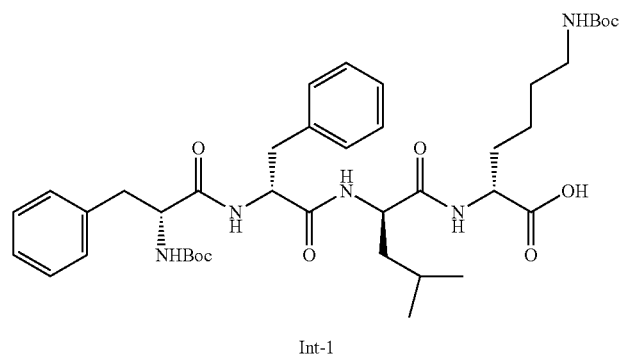
Int-1

The general synthesis scheme used in the preparation of boronic acid intermediates Int-2, Int-3 and Int-4 was as follows:
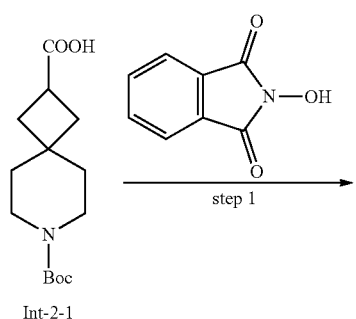
Int-2-1
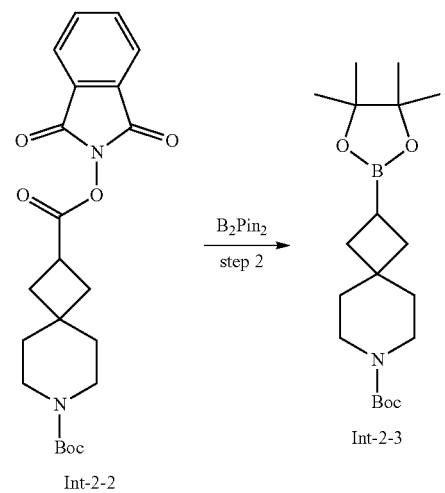
Int-2
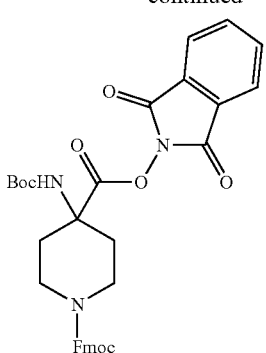
Int-3-2
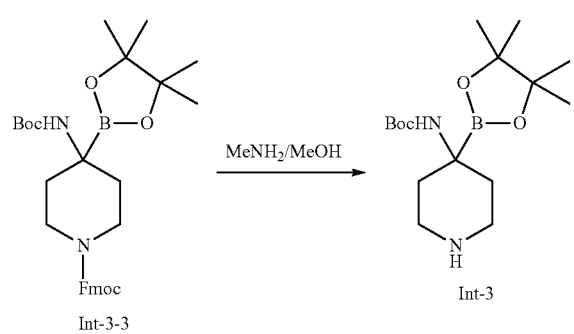
Int-3-3    Int-3
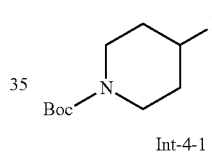
Int-4-1
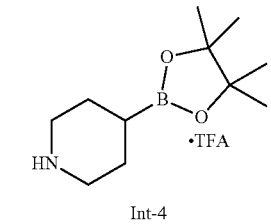
Int-4
The preparation scheme of boronic acid intermediates Int-5 was as follows:
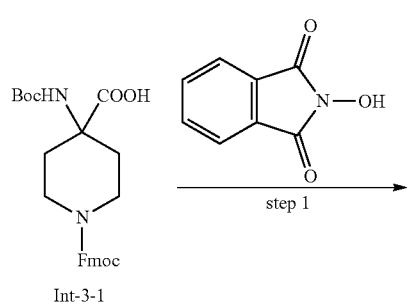
Int-3-1
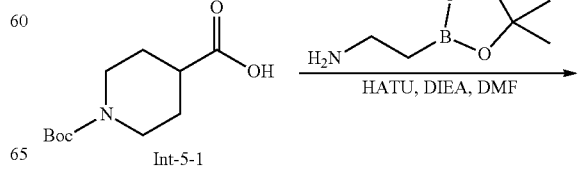
Int-5-1

43
-continued
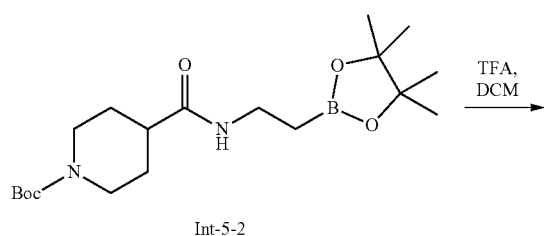
Int-5-2
44
-continued
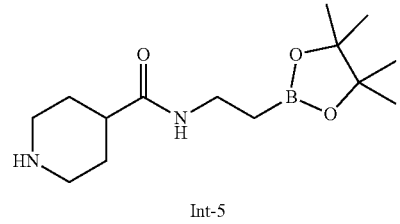
Int-5
The general synthesis scheme used in the preparation of target compounds TM-1 to TM-36 was shown as follows:
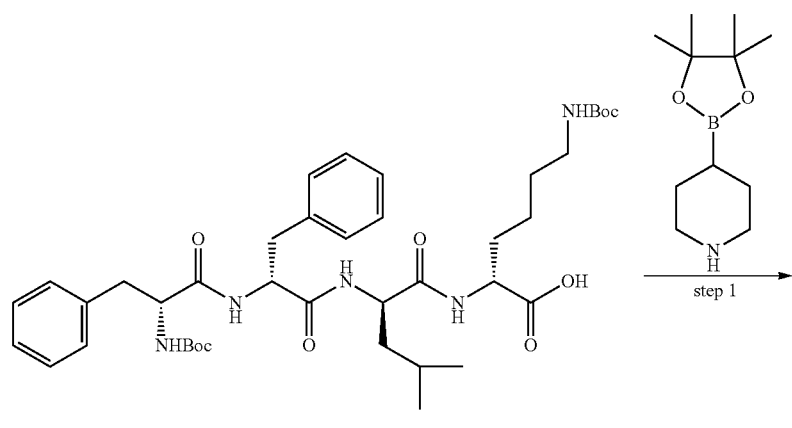
Int-1
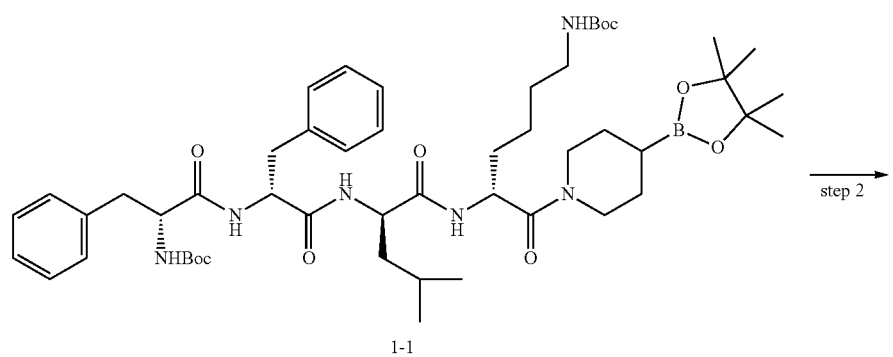
1-1
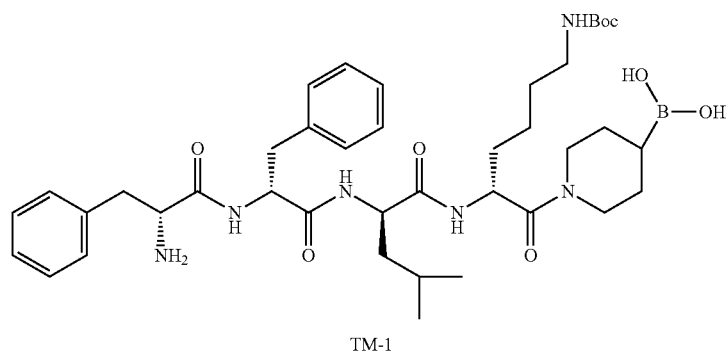
TM-1

The general synthesis scheme used in the preparation of target compounds TM-10, 11, 16, 17 and 29 was shown as follows:

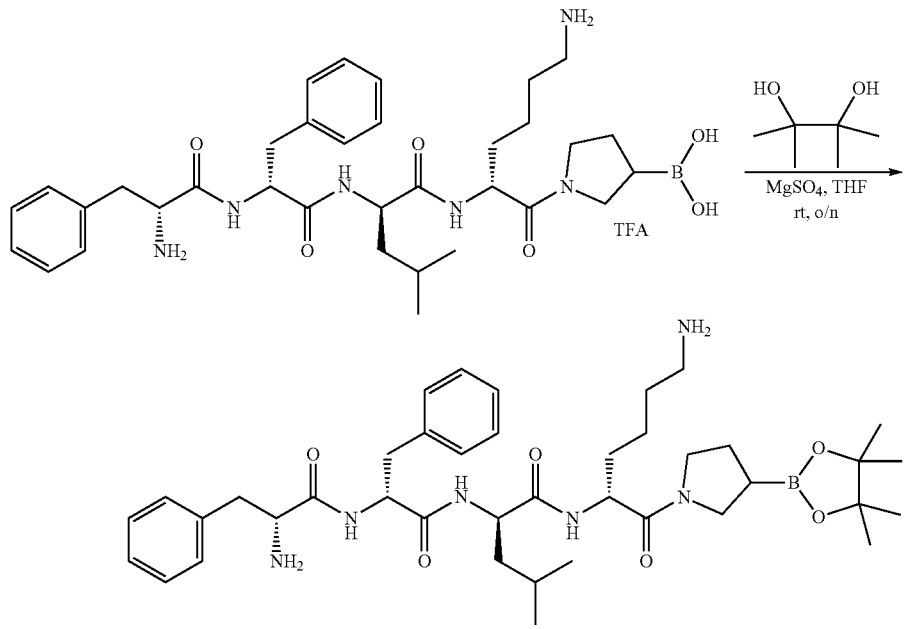

The meanings of the abbreviations of the materials used in the present invention were shown in Table 1:

| English abbreviation | Full name |
| --- | --- |
| Boc | tert-butyloxycarbonyl |
| Fmoc | fluorenylmethoxycarbonyl |
| DIEA | diisopropylethylamine |
| HBTU | O-(benzotriazol-1-yl)-N,N,N,N-tetramethyluroniumhexafluorophosphate |
| HOBt | 1-hydroxybenzotriazole |
| DIC | N,N'-diisopropylcarbodiimide |
| DCM | dichloromethane |
| 2-CTC Resin | 2-chlorotritylchloride resin |
| DMF | N,N-dimethylformamide |
| LCMS | liquid chromatography-mass spectrometer |
| hKOR | Human κ-opioid receptor |
| DOR | δ-opioid receptor |
| MOR | μ-opioid receptor |

Biological evaluation of some polypeptide derivatives prepared in the above examples were carried out.

1. Agonistic activity and selectivity of the κ-opioid receptors

Forskolin can stimulate the release of cAMP from HEK293 cells with high expression of human κ (or μ, or δ)-opioid receptors. The κ-opioid receptor agonists can inhibit the release of cAMP from the HEK293 cells with high expression of human κ-opioid receptors stimulated by Forskolin, but do not affect the release of cAMP from the HEK293 cells with high expression of human μ (or δ)-opioid receptors stimulated by Forskolin. The efficacy of the compounds of the invention as κ-opioid receptor agonists was determined by measuring the ability of the compounds of Examples to inhibit adenylate cyclase activity.

Cell culture: The HEK293 cell line highly expressing human κ (or μ, or δ)-opioid receptor were cultured in DMEM medium containing 10% FBS.

Stimulation: the test compound was 4-fold diluted in a gradient manner to obtain 10 concentrations, and 50 nl of each was transferred to a 384-well plate, and then 10 nl Forskolin was added; the cells were digested, re-suspended, and counted; and then 10 μl of cell suspension ($5\times10^5$ cell/mL) was added, and the cells were mixed gently, and incubated at 23° C. for 60 minutes.

Detection: cAMP Assay Kit (Cisbio) was used, cAMPD2 and Anti-cAMP conjugate were added, and the resultant mixture was incubated for 1 h at room temperature. The plate was read using envision (Perkin Elmer) and $EC_{50}$ was obtained by means of fitting with a four-parameter equation.

Experimental results: As shown in Table 2, the agonistic activity ($EC_{50}$) of all the tested compounds are below the nM level, and they have excellent selectivity for the κ-opioid receptor.

TABLE 2

Agonistic activity and selectivity of the compounds on κ-opioid receptors ($EC_{50}$)

| Compounds | KOR ($EC_{50}$, nM) | DOR ($EC_{50}$, nM) | MOR ($EC_{50}$, nM) |
| --- | --- | --- | --- |
| TM-1 | 0.0984 | >10000 | >10000 |
| TM-2A | 0.0331 | >10000 | >10000 |
| TM-3 | 0.0547 | >10000 | >10000 |
| TM-5 | 0.0270 | >10000 | >10000 |
| TM-7 | 0.0087 | >10000 | >10000 |
| TM-8 | 0.0846 | >10000 | >10000 |
| TM-9A | 0.0012 | >10000 | >10000 |
| TM-13A | 0.0946 | >10000 | >10000 |
| TM-22B | 0.0095 | >10000 | >10000 |
| TM-26 | 0.0082 | >10000 | >10000 |

2. Inhibition of Cytochrome $P_{450}$ Oxidase

The human liver microsomes (0.253 mg/mL protein) containing cytochrome $P_{450}$, test compounds (0.05-50 μM), CYPs substrates (10 μM p-acetaminophen, 5 μM diclofenac, 30 μM mephenytoin, 5 μM dextromethorphan hydrobromide, 2 μM midazolam), 1.0 mM NADP were incubated at 37° C. for 10 minutes. Naflavone, sulfafenpyrazole, N-3-benzylnivan, quinidine, and ketoconazole were used as reference inhibitors. The results are shown in Table 3. The $IC_{50}$ of the test compounds are all greater than 50 μM.

TABLE 3

Inhibitory activity ($IC_{50}$) of the compounds on cytochrome $P_{450}$ CYP isoenzyme

| | CYPs | | | | |
|---|---|---|---|---|---|
| Compounds | 1A2 (μM) | 2D6 (μM) | 3A4 (μM) | 2C9 (μM) | 2C19 (μM) |
| TM-2A | >50 | >50 | >50 | >50 | >50 |
| TM-3 | >50 | >50 | >50 | >50 | >50 |
| TM-8 | >50 | >50 | >50 | >50 | >50 |
| TM-9A | >50 | >50 | >50 | >50 | >50 |
| TM-22B | >50 | >50 | >50 | >50 | >50 |
| TM-26 | >50 | >50 | >50 | >50 | >50 |

3. Membrane Permeability of the Compounds

The Caco-2 cell line is a human colon adenocarcinoma cell line that differentiates in culture and is used to model the epithelial lining of the human small intestine. Compounds of the present invention were tested in a membrane permeability assay using Caco-2 cell membrane layer in a standard assay. The apparent permeability coefficient (Papp) can be determined in the apical-to-basolateral (A-B) direction across cell monolayers cultured on 96-well polycarbonate membrane filters. The compound was maintained at pH 7.4 on the acceptor side at a concentration of 5 μM, and the test plate was gently shaken and incubated at 37° C. for 120 minutes. Samples were taken at time zero from the donor side and at the end of the incubation period from both the donor and acceptor sides. Samples were analyzed by HPLC-MS/MS. The Papp value (expressed as $10^6$ cm/sec) was then calculated based on the appearance rate of compound on the recipient side. Papp can be calculated by the following equation:

$$Papp = (VA \times [drug]_{acceptor}) / (Area \times Time \times [drug]_{initial, donor})$$

wherein Papp is the apparent permeability; VA is the volume of the acceptor side, Area is the surface area of the membrane, $[drug]_{initial, donor}$ is the concentration on the donor side at time zero, $[drug]_{acceptor}$ is the concentration of the compounds on the recipient side at the end of the incubation period, Time is the total incubation time.

TABLE 4 membrane permeability of the compounds

| Compounds | Mean permeability (Papp) ($10^{-6}$, cm/s) |
|---|---|
| TM-2A | <0.05 |
| TM-3 | <0.20 |
| TM-8 | <0.10 |
| TM-9A | <0.05 |
| TM-22B | <0.10 |
| TM-26 | <0.10 |

4. Acetic Acid Writhing Test in Mice

The analgesic effect of the compound of the invention was evaluated by measuring the analgesic $ED_{50}$ of the compounds of Examples in the acetic acid writhing test in mice.

The ICR male mice (18-25 g) were randomly separated into the drug group and the model group. 15 minutes after IV administration, 0.6% (v/v) acetic acid solution was intraperitoneally injected at 10 mL/kg. The number of writhes of the mice within 15 min was counted. The inhibition rate on the writhes was calculated based on the number of writhes. The $ED_{50}$ of the compound to be tested was calculated based on inhibition rate according to a four-parameter equation.

| Compounds | $ED_{50}$ (μg/kg) |
|---|---|
| TM-2A | 0.679 |
| TM-9A | 0.377 |

The specific embodiments described above further describe the purpose, technical solutions and beneficial effects of the present invention in detail. It should be understood that the above descriptions are only specific embodiments of the present invention and are not intended to limit the scope of the present invention. Any modification, equivalent replacement, or improvement made within the spirit and principle of the present invention shall be included in the protection scope of the present invention.

The invention claimed is:

1. A polypeptide compound selected from the group consisting of

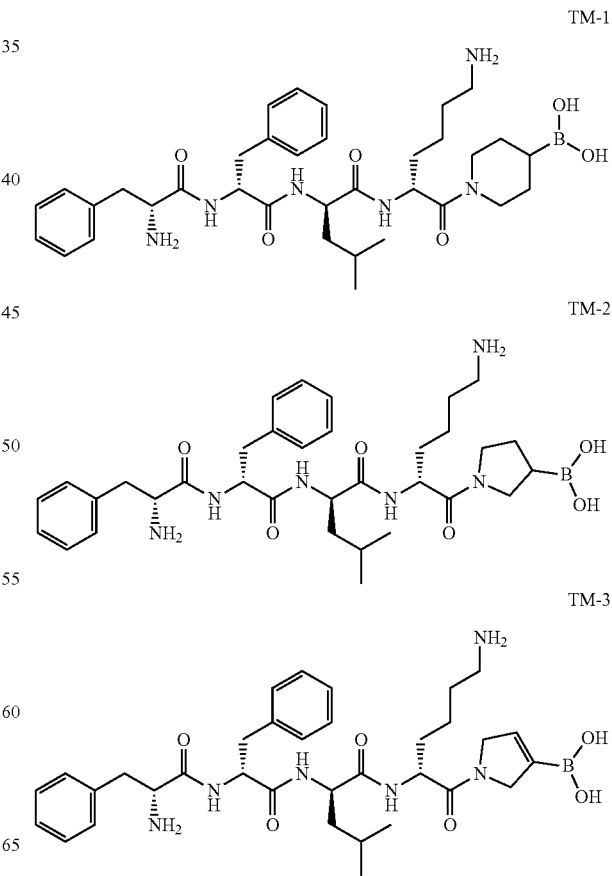

TM-4
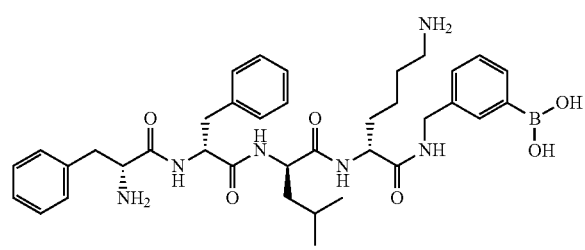
TM-5
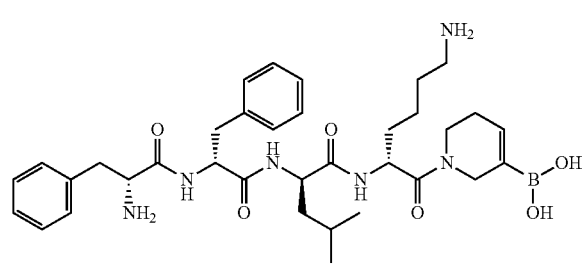
TM-6
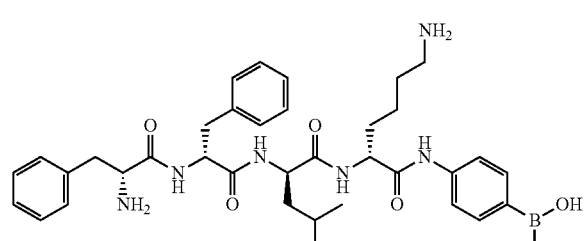
TM-7
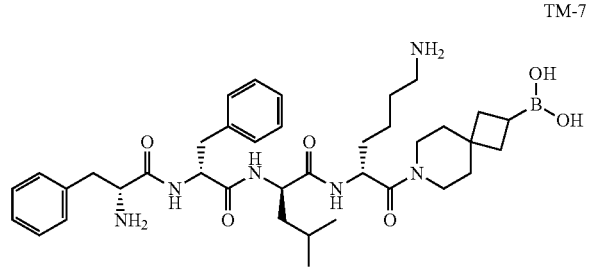
TM-8
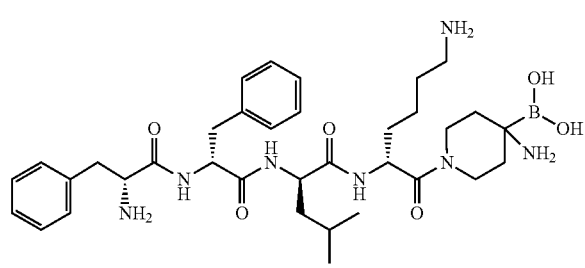
TM-9
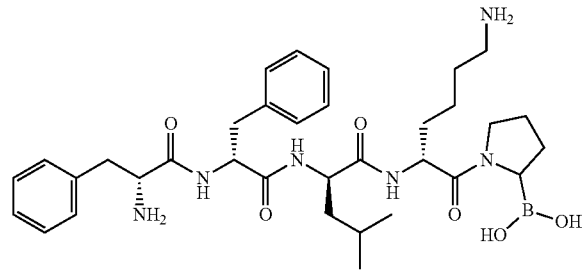
TM-10
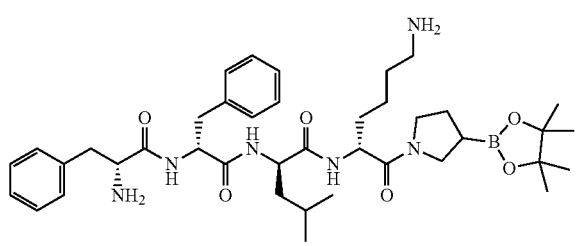
TM-11
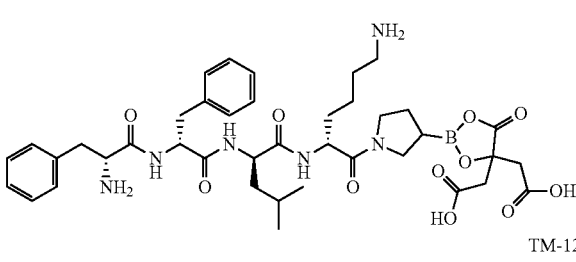
TM-12
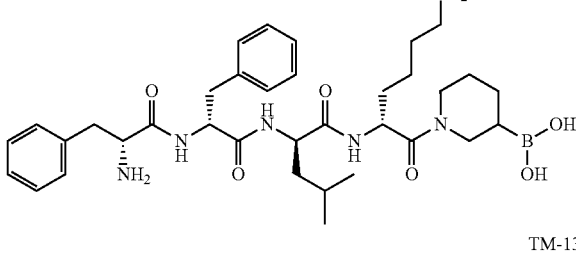
TM-13
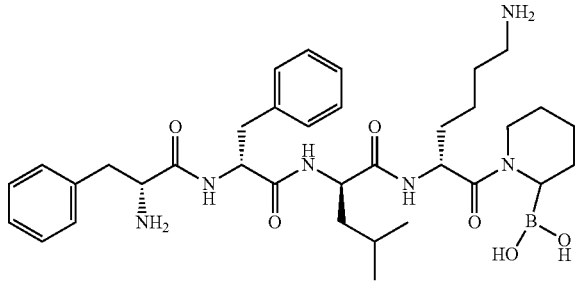
TM-14
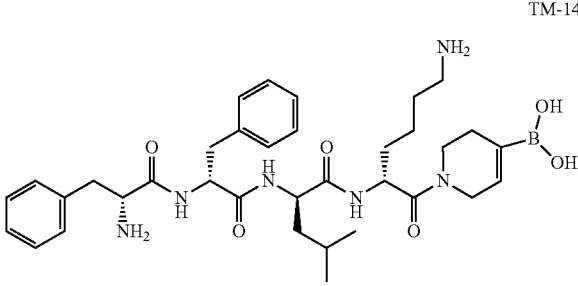
TM-15
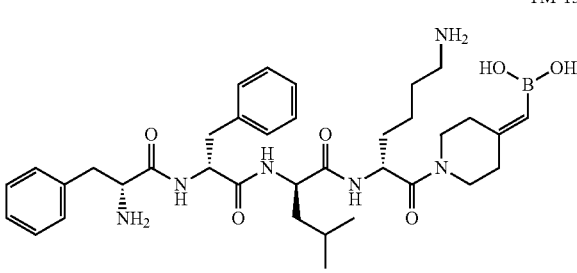

TM-16
TM-17
TM-18
TM-19
TM-20
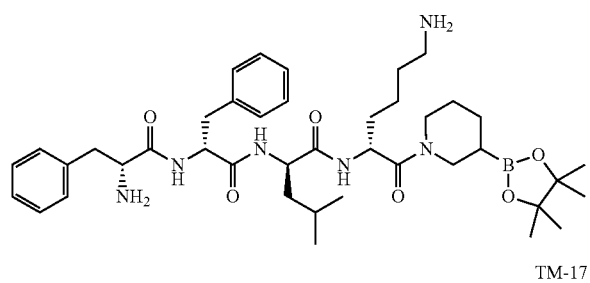
TM-21
TM-22
TM-23
TM-24
TM-25
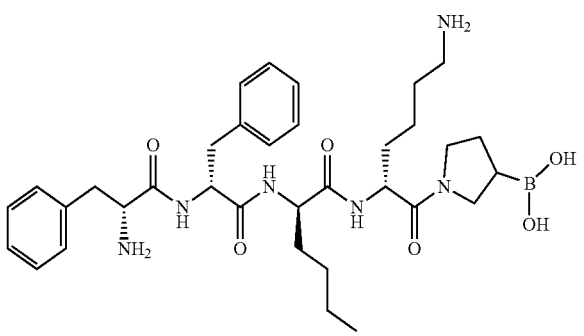
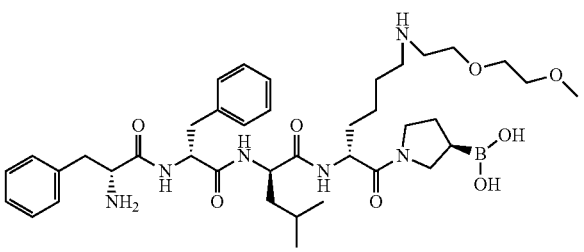
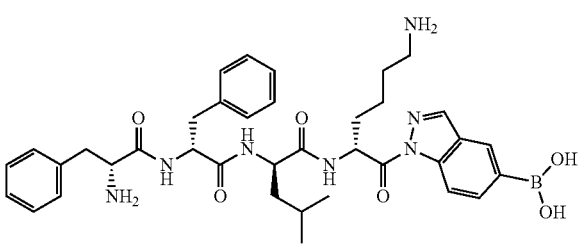
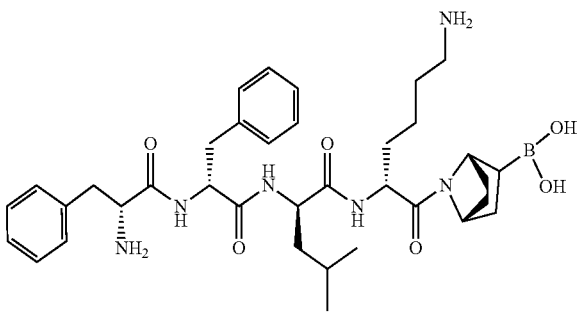
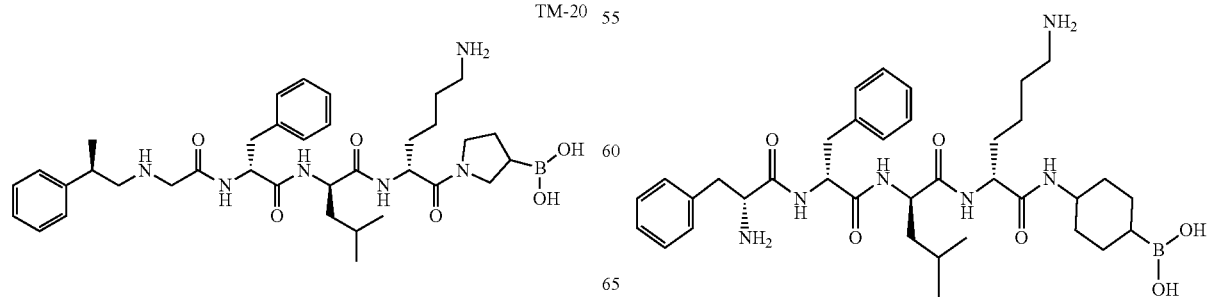

TM-26
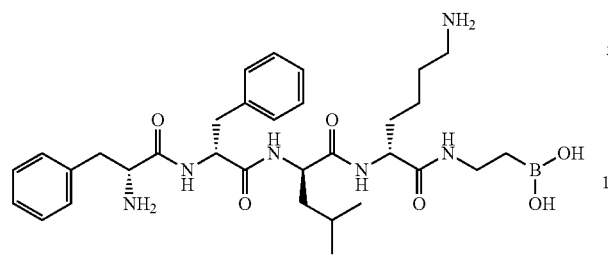
TM-31
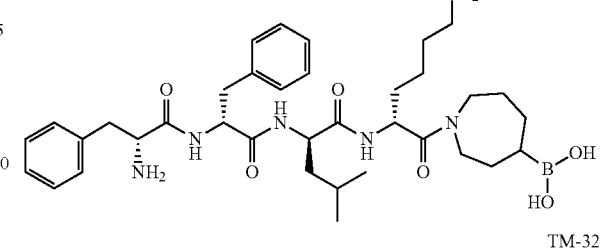
TM-27
TM-32
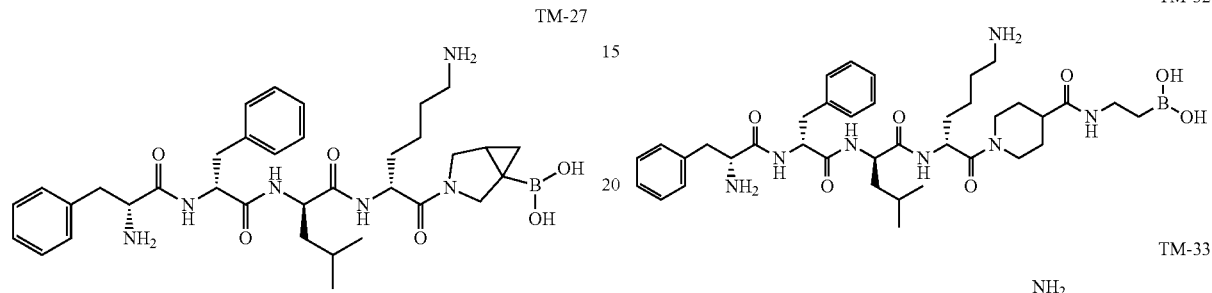
TM-33
TM-28
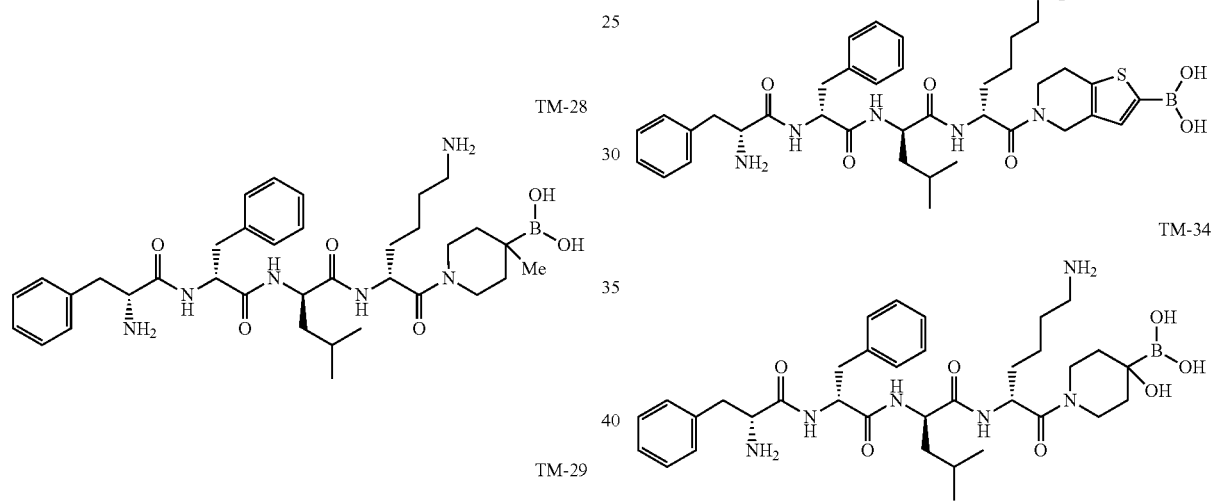
TM-34
TM-29
TM-35
TM-30
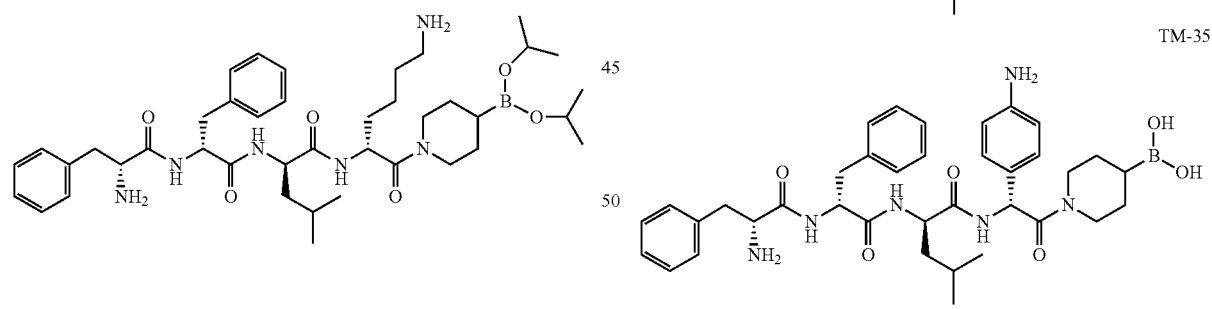
TM-36
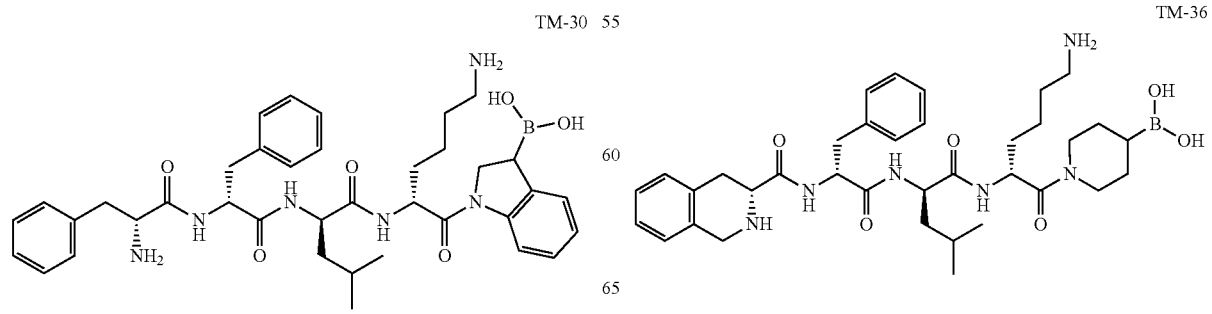
or pharmaceutically acceptable salts thereof.

2. A pharmaceutical composition comprising the polypeptide compound or pharmaceutically acceptable salts thereof according to claim 1.

* * * * *